United States Patent
Feher et al.

(10) Patent No.: US 6,852,858 B2
(45) Date of Patent: Feb. 8, 2005

(54) PROCESS FOR PURIFYING N-[3-(3-CYANOPYRAZOLO[1,5-A]PYRIMIDIN-7-YL)PHENYL]-N-ETHYLACETAMIDE (ZALEPLON) AND CRYSTALLINE FORMS OF ZALEPLON ACCESSIBLE WITH THE PROCESS

(75) Inventors: Erika Feher, Debrecen (HU); Ferenc Korodi, Debrecen (HU); Claude Singer, Kafar Saba (IL); Erika Magyar, Debrecen (HU)

(73) Assignee: Biogal Gyogyszergyar Rt., Debrecen (HU)

(*) Notice: Subject to any disclaimer, the term of this patent is extended or adjusted under 35 U.S.C. 154(b) by 0 days.

(21) Appl. No.: 10/211,461

(22) Filed: Aug. 1, 2002

(65) Prior Publication Data

US 2003/0130291 A1 Jul. 10, 2003

Related U.S. Application Data

(63) Continuation-in-part of application No. 10/170,673, filed on Jun. 12, 2002.
(60) Provisional application No. 60/388,199, filed on Jun. 12, 2002, provisional application No. 60/309,391, filed on Aug. 1, 2001, and provisional application No. 60/317,907, filed on Sep. 6, 2001.

(51) Int. Cl.$^7$ ............ C07D 487/04; A61K 31/519; G01N 33/15
(52) U.S. Cl. ............ 544/281; 436/98
(58) Field of Search ............ 514/259.3; 544/281; 436/98

(56) References Cited

U.S. PATENT DOCUMENTS 4,626,538 A   12/1986   Dusza
5,714,607 A   2/1998    Padmanathan

FOREIGN PATENT DOCUMENTS

WO    WO 200212244 A2 *  2/2002   ......... A61K/31/519

OTHER PUBLICATIONS

Mustazza, J. Het. Chem. 38, 1119 (2001).*

* cited by examiner

*Primary Examiner*—Mark L. Berch
(74) *Attorney, Agent, or Firm*—Kenyon & Kenyon

(57) ABSTRACT

Zaleplon can be separated from a regioisomer impurity by crystallization from selected solvents or by adding an anti-solvent to a solution of zaleplon and the regioisomer. Zaleplon crystalline Forms II, III, IV, and V are useful for the treatment of insomnia. These crystalline Forms are described along with processes for making them v crystallization from selected solvents.

19 Claims, 10 Drawing Sheets

PROCESS FOR PURIFYING N-[3-(3-CYANOPYRAZOLO[1,5-A]PYRIMIDIN-7-YL)PHENYL]-N-ETHYLACETAMIDE (ZALEPLON) AND CRYSTALLINE FORMS OF ZALEPLON ACCESSIBLE WITH THE PROCESS

CROSS-REFERENCE TO RELATED APPLICATIONS

This application is a continuation-in-part of U.S. patent application Ser. No. 10/170,673, filed Jun. 12, 2002, which claims the benefit of U.S. Provisional Patent Application Ser. No. 60/297,635, filed on Jun. 12, 2001. This application also claims the benefit of U.S. Provisional Patent Applications Ser. Nos. 60/309,391, filed Aug. 1, 2001; 60/317,907, filed Sep. 6, 2001 and 60/388,199, filed Jun. 12, 2002. All of these applications are incorporated herein by reference.

FIELD OF THE INVENTION

The present invention relates to the anxiolytic, antiepileptic, sedative, hypnotic, and skeletal muscle relaxing agent zaleplon. More particularly, the invention relates to late stage processing of zaleplon and to particular crystal forms of the drug accessible by adjustments in the late stage processing. The invention further relates to N-[3-(3-cyanopyrazolo[1,5-a]pyrimidin-5-yl)phenyl]-N-ethylacetamide (4), regioisomer of zaleplon. The invention further relates to HPLC methods for the analysis and assay of zaleplon.

BACKGROUND OF THE INVENTION

Zaleplon possesses anxiolytic, antiepileptic, sedative and hypnotic properties. It is approved by the U.S. Food and Drug Administration for short-term treatment of insomnia and is available by prescription under the brand name Sonata®. The molecular structure of zaleplon is known and may be represented as:

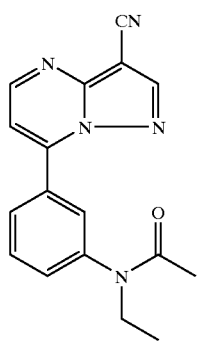

The IUPAC name of zaleplon is N-[3-(3-cyanopyrazolo[1,5-a]pyrimidin-7-yl)phenyl]-N-ethylacetamide.

U.S. Pat. No. 4,626,538 ("the '538 patent") provides a general methodology for preparing zaleplon and structurally related compounds. In Example 2 of the '538 patent, N-(3-acetylphenyl)ethanamide 1 is reacted with dimethylformamide dimethyl acetal to form N-[3-[3-(dimethylamino)-1-oxo-2-propenyl)]phenyl]-N-acetamide 2. In Example 7 of the '538 patent, the primary amide of acetamide 2 is alkylated with ethyl iodide, forming N-[3-[3-(dimethylamino-1-oxo-2-propenyl]phenyl]-N-ethylacetamide 3. Zaleplon was prepared in Example 14 by condensing ethylacetamide 3 and 3-amino-4-cyanopyrazole 4 in refluxing glacial acetic acid. Zaleplon was worked up by partitioning the non-volatiles between saturated sodium bicarbonate and dichloromethane, drying the organic phase, passing the organic phase through an adsorbent (magnesium silicate), adding hexane to the organic phase, cooling the organic phase and collecting a solid that forms in the organic phase. The product is reported to have a melting point of 186–187° C. The overall synthesis is depicted in Scheme 1. The '538 patent does not indicate that byproducts were formed in any of the reactions or explain how byproducts could be separated from zaleplon if they did form.

Scheme 1

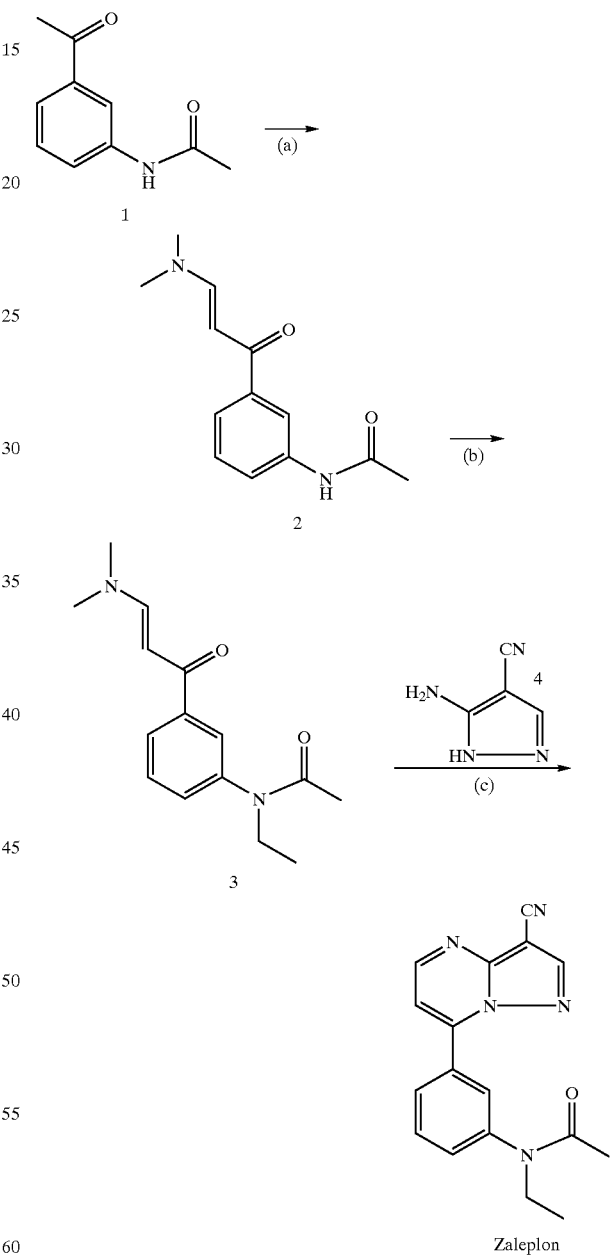

(a) dimethylformamide dimethyl acetal, refl.; (b) ethyl iodine, sodium hydride, DMF; (c) glacial acetic acid, refl.

U.S. Pat. No. 5,714,607 ("the '607 patent") describes an improved process for preparing zaleplon. According to the '607 patent, zaleplon can be obtained in improved yield and purity if the final step of the '538 patent process is modified by adding water to the acetic acid solvent at about 10% to about 85% (v/v). As stated in the '607 patent, the improved conditions shorten the reaction time from about 3–3.5 h to about 1–3.5 hours. According to Table 1 of the '607 patent, zaleplon was obtained in yields ranging from 81.7–90% and in HPLC purity ranging from 98.77 to 99.4%. In each of the examples, zaleplon was obtained by crystallization out of the reaction mixtures, which were mixtures of water and acetic acid. The '538 patent does not indicate that byproducts were formed in the process or explain how byproducts could be separated from zaleplon if they were to form.

Commonly assigned co-pending U.S. patent application Ser. No. 10/170,673 discloses a process for preparing zaleplon by condensing N-ethylacetamide 3 and pyrazole 4 or their acid addition salts in a reaction medium comprising water and a water-miscible organic compound.

United States patent application Ser. No 10/170,673, filed Jun. 12, 2002, is hereby incorporated by reference in its entirety.

In order to obtain marketing approval for a new drug product, manufacturers have to submit to the regulatory authorities evidence to show that the product is acceptable for human administration. Such a submission must include, among other things, analytical data to show the impurity profile of the product to demonstrate that the impurities are absent, or are present only a negligible amount. For such a demonstration there is a need for analytical methods capable of detection of the impurities and reference standards for identification and assaying thereof. There is also a need for reference standards in such analytical methods.

The U.S. Food and Drug Administration's Center for Drug Evaluation and Research (CDER) has promulgated guidelines recommending that new drug and generic drug applicants identify organic impurities of 0.1% or greater in the active ingredient. "Guideline on impurities in New Drug Substances" 61 Fed. Reg. 371 (1996), "Guidance for Industry ANDAs: Impurities in Drug Substances" 64 Fed. Reg. 67917 (1999). Unless an impurity is a human metabolite, has been tested for safety, or was present in a composition that was shown to be safe in clinical trials, the CDER further recommends that the drug applicant reduce the amount of the impurity in the active ingredient to below 0.1%. Thus, there is a need to isolate impurities in drug substances so that their pharmacology and toxicology can be studied.

Crystalline forms, that include polymorphs and pseudopolymorphs, are distinct solids sharing the same structural formula, yet having different physical properties due to different conformations and/or orientations of the molecule in the unit cell. One physical property that can vary between crystalline forms is solubility, which can affect the drug's bioavailability. Crystalline forms of a compound can be differentiated in a laboratory by powder X-ray diffraction spectroscopy. For a general review of crystalline forms (i.e. polyrnorphs and pseudopolymorphs) and the pharmaceutical applications of polymorphs see G. M. Wall, Pharm Manuf 3,33 (1986); J. K. Haleblian and W. McCrone, J. Pharm. Sci., 58, 911 (1969); and J. K. Haleblian, J. Pharm. Sci., 64, 1269 (1975).

The discovery of new crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. The present invention provides four new crystalline forms of zaleplon.

SUMMARY OF THE INVENTION

Figure 1:
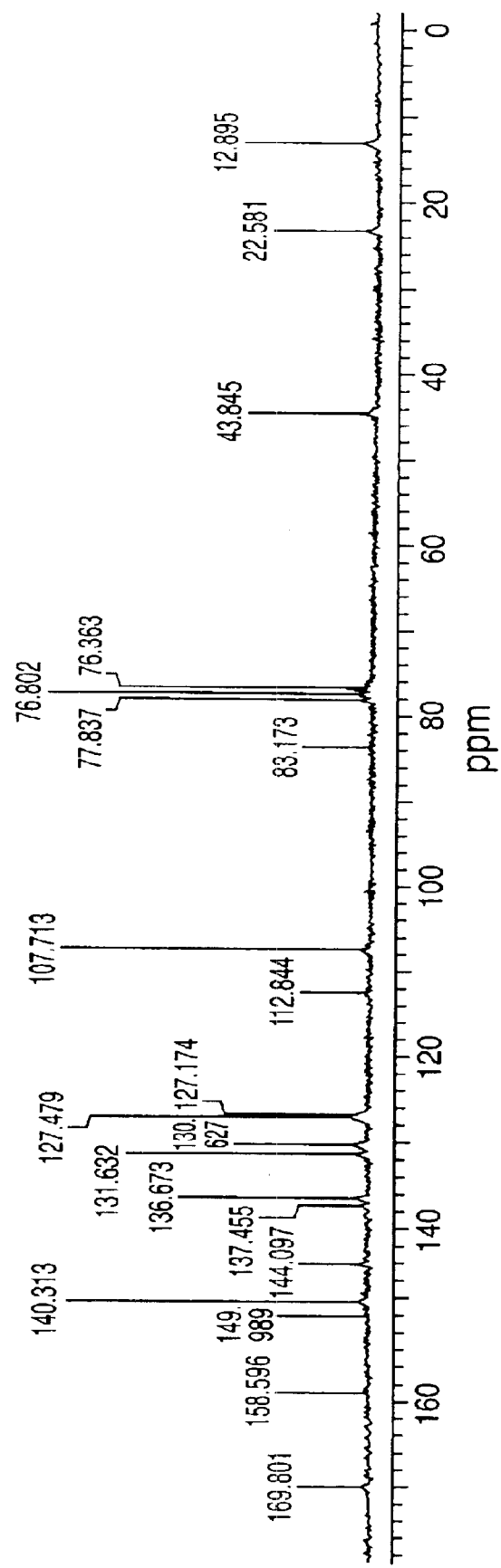
FIG. 1 is a representative 13C NMR spectrum for the zaleplon regioisomer.

N-[3-(3-cyanopyrazolo[1,5-a]pyrimidin-5-yl)phenyl]-N-ethylacetamide 5 having the structural formula

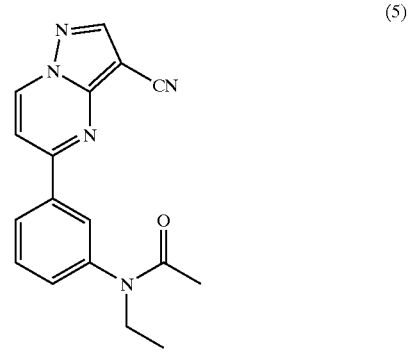

(5)

forms as a minor byproduct in the condensation step of the reaction disclosed in U.S. patent application Ser. No. 10/170,673. This compound is previously unknown in the chemical literature and, as discussed below, it can serve as a reference standard in the analysis of zaleplon. Compound 5 is a regioisomer of zaleplon that differs from zaleplon in the position of the N-ethyl-N-acetylaminophenyl group on the fused heterocyclic ring system. The formation of regioisomer 5 can be accounted for by either (1) a 1,2 addition of the 3-amino group of cyanopyrazole 4 with elimination of water and Michael-type addition of the 2-nitrogen atom of the pyrAzole onto the conjugated C=C double bond or (2) a Michael addition of the 2-nitrogen atom of the pyrazole and cyclization of the 3-amino group onto the keto group. By whatever mechanism regioisomer 5 forms, the salient fact is that it is an undesired minor byproduct in viable commercial preparations of zaleplon.

Under the conditions set forth in the Ser. No. 10/170,673 patent application, regioisomer 5 typically forms to the extent of about 0.2 to 0.5% relative to the desired isomer.

Thus, in one aspect, the present invention relates to N-[3-(3-cyanopyrazolo[1,5a]pyrimidin-5-yl)phenyl]-N- ethylacetamide, which is referred to as zaleplon regioisomer or regioisomer of zaleplon.

In another aspect, the present invention relates to a method of making N-[3-(3-cyanopyrazolo[1,5-a]pyrimidin-5-yl)phenyl]-N-ethylacetamide including the steps of reacting a mixture of N-[3-[3-(dimethylamino)-1-oxo-2-propenyl]phenyl]-N-ethylacetamide, 3-amino-4-cyanopyrazole, and a strong acid in a liquid reaction medium of water and at least one water-miscible organic compound free of carboxylic acid groups, neutralizing the reaction mixture to precipitate crude product, and separating N-[3-(3-cyanopyrazolo[1,5-a]pyrimidin-5-yl)phenyl]-N-ethylacetamide from other components of crude product by chromatography on a silica gel column using a mixture of chloroform and acetone as eluent, wherein the amount of strong acid, on a mole basis, is at least 10 times the amount of either N-[3-[3-(dimethylamino)-1-oxo-2-propenyl]phenyl]-N-ethylacetamide or 3-amino-4-cyanopyrazole, whichever is in excess, or of either of them if they are used in approximately equimolar amounts.

In another aspect, the present invention relates to a method of making N-[3-(3-cyanopyrazolo[1,5-a]pyrimidin-5-yl)phenyl]-N-ethylacetamide comprising the steps of reacting a mixture of N-[3-[3-(dimethylamino)-1-oxo-2-propenyl]phenyl)-N-ethylacetamide, 3-amino-4-cyanopyrazole, and a strong acid in a liquid reaction medium of water and at ]cast one water-miscible organic compound free of carboxylic acid groups, neutralizing the reaction mixture to precipitate crude product, and separating N-[3-(3-cyanopyrazolo[1,5-a]pyrimidin-5-yl)phenyl]-N-ethylacetamide from other components of crude product by chromatography on a silica gel column using a mixture of chloroform and acetone as eluent, wherein the amount of strong acid, on a mole basis, is at least 20 times the amount of either N-[3-[3-(dimethylamino)-1-oxo-2-propenyl]phenyl]-N-ethylacetamide or 3-amino-4-cyanopyrazole, whichever is in excess, or of either of them if they are used in approximately equimolar amounts.

Zaleplon and regioisomer 5 are difficult to separate because of their structural similarity. There is a need in the pharmaceutical arts for a process of purifying zaleplon that is in mixture with the regioisomer. The present invention meets this need with a precipitation process that is effective at separating the two compounds. It will be understood that the present method of purifying zaleplon is effective in reducing or eliminating many other impurities as well.

Thus, in another aspect, the present invention provides a process for purifying zaleplon, for example crude zaleplon, that can be in mixture with zaleplon regioisomer and other impurities by precipitating a solid enriched in zaleplon from a solution formed from a crude zaleplon from any source. The solution can be formed by dissolving crude zaleplon obtained from any source in an organic solvent at elevated temperature. Purified zaleplon can be precipitated from the solution by cooling the solution from the elevated temperature, by use of an anti solvent, or by use of an antisolvent and cooling. In one embodiment of the process, an antisolvent is added to the solution at elevated temperature. By means of the purification process, zaleplon essentially free of regioisomers can be obtained.

In another aspect, the present invention provides a process for purifying zaleplon that can be in mixture with zaleplon regioisomer and other impurities by precipitating a solid enriched in zaleplon from a solution formed from a crude zaleplon from any source. The solution can be formed by dissolving crude zaleplon in an organic solvent at elevated temperature, wherein the organic solvent is selected from the group consisting of alcohols, ketones, ethers, carboxylic acids, carboxylic acid esters, nitrites, aromatic hydrocarbons, and halogenated hydrocarbons, mixtures of any of them, and mixtures of one or more of them with water. Purified zaleplon can be precipitated from the solution by cooling the solution from the elevated temperature, by use of an anti solvent, or by use of an antisolvent and cooling. In one embodiment of the process, an antisolvent is added to the solution at elevated temperature. By means of the purification process, zaleplon essentially free of regioisomer and other impurities can be obtained.

In still another aspect, the present invention provides a process for purifying zaleplon that can be in mixture with zaleplon regioisomer and other impurities by precipitating a solid enriched in zaleplon from a solution formed from a crude zaleplon from any source. The solution can be formed by dissolving crude zaleplon in an organic solvent at elevated temperature, wherein the organic solvent is selected from the group consisting of methanol, ethanol, 2-propanol, acetone, methyl ethyl ketone, methyl isobutyl ketone, tetrahydrofuran, diethyl ether, methyl t-butyl ether, acetic acid, propionic acid, ethyl acetate, isobutyl acetate, acetonitrile, acrylonitrile, benzene, toluene, xylenes, dichloromethane and chloroform. Purified zaleplon can be precipitated from the solution by cooling the solution from the elevated temperature, by use of an anti solvent, or by use of an antisolvent and cooling. In one embodiment of the process, an antisolvent is added to the solution at elevated temperature. By means of the purification process, zaleplon essentially free of regioisomer and other impurities can be obtained.

In another aspect, the present invention provides a process for purifying zaleplon that can be in mixture with zaleplon regioisomer and other impurities by precipitating a solid enriched in zaleplon from a solution formed from a crude zaleplon. The solution can be formed by dissolving crude zaleplon in an organic solvent at elevated temperature and can have a concentration between about 100 mM and about 1 M. Purified zaleplon can be precipitated from the solution by cooling the solution from the elevated temperature, by use of an antisolvent, or by use of an antisolvent and cooling.

Thus, in another aspect, the present invention provides a process for purifying zaleplon that can be in mixture with zaleplon regioisomer and other impurities by precipitating a solid enriched in zaleplon from a solution formed from a crude zaleplon from any source. The solution can be formed by dissolving crude zaleplon in an organic solvent (especially acetic acid, methanol ethanol, 2-propanol, tetrahydrofuran, acetonitrile, or acetone) at elevated temperature. Antisolvent (especially water) is added whilst the solution is at the elevated temperature. Purified zaleplon can be precipitated from the solution by cooling the solution from the elevated temperature, by use of an anti solvent, or by use of an antisolvent and cooling. In one embodiment of the process, an antisolvent is added to the solution at elevated temperature.

In still another aspect, the present invention provides a process for purifying zaleplon that can be in mixture with zaleplon regioisomer and other impurities by precipitating a solid enriched in zaleplon from a solution formed from a crude zaleplon from any source. The solution can be formed by dissolving crude zaleplon in an organic solvent at elevated temperature. Purified zaleplon can be precipitated from the solution by cooling the solution from the elevated temperature, by use of an antisolvent, or by use of an antisolvent and cooling. In one embodiment of the process, an antisolvent is added to the solution at elevated temperature. By means of the purification process, zaleplon having at least about 50%, and as much as about 70%, less zaleplon regioisomer compared to the crude zaleplon used as starting material in the process is obtained.

In another aspect, the present invention provides a process for purifying zaleplon that can be in mixture with zaleplon regioisomer and other impurities by precipitating a solid enriched in zaleplon from a solution formed from a crude zaleplon from any source The solution can be formed by dissolving crude zaleplon in an organic solvent selected, from acetonitrile and ethanol, at elevated temperature. Antisolvent is added whilst the solution is at the elevated temperature. When acetonitrile is the solvent, wafer is the antisolvent. When ethanol is the solvent, hexane is the antisolvent. Purified zaleplon can be precipitated from the solution by cooling the solution from the elevated temperature.

In another aspect, the present invention relates to a process for purifying zaleplon including the steps of: forming a solution of a solid comprising zaleplon in ethanol, precipitating a solid enriched in zaleplon, relative to the solid comprising zaleplon used to make the solution, with the use of an antisolvent that is water, isolating the precipitated solid that is enriched in zaleplon, forming a solution of the precipitated sold enriched in zaleplon of step in ethanol, precipitating from the solution of the immediately preceeding step, without the aid of an antisolvent, a solid further enriched in zaleplon, and isolating the solid further enriched in zaleplon of step.

Characterization of the essentially pure zaleplon obtained from the purification process led to the discovery that certain process embodiments produce novel crystalline forms of zaleplon, wherefor the present invention further provides novel crystalline forms of zaleplon that are accessible by the stepwise procedure of the purification process by appropriate selection of solvent, antisolvent and/or other conditions.

Thus, in one aspect, the present invention provides crystalline zaleplon Form II characterized by a powder X-ray diffraction pattern having peaks at 7.9, 10.7, 12.5, 14.9, 16.9, 17.9, 21.3, 24.0, 25.2, 25.9, 27.0 and 27.5±0.2 degrees two-theta.

In another aspect, the present invention provides crystalline zaleplon Form III characterized by a powder X-ray diffraction pattern having peaks at 15.4, 18.1, 21.1, 26.8, and 27.5±0.2 degrees two-theta.

In yet another aspect, the present invention provides crystalline zaleplon Form III characterized by a powder X-ray diffraction pattern having peaks at 15.4, 18.1, 21.1, 26.8, and 27.5±0.2 degrees two-theta and further characterized by x-ray diffraction peaks (reflections) at 11.6, 17.6, 19.0, 20.0, and 22.2 degrees two-theta.

In still a further aspect, the present invention provides crystalline zaleplon Form IV characterized by a powder X-ray diffraction pattern having peaks at 8.1, 14.5, 17.3, 21.3±0.2 degrees two-theta.

In another aspect, the present invention provides crystalline zaleplon Form IV characterized by a powder X-ray diffraction pattern having peaks at 8.1, 14.5, 17.3, 21.3±0.2 degrees two-theta and further characterized by by x-ray diffraction peaks at 10.6, 11.1, 14.1, 15.6, 18.0, 18.2, 20.1, 20.3, 24.3, 25.0, 25.9, 26.7, 27.9 and 29.5±0.2 degrees two-theta.

In still another aspect, the present invention relates to crystalline zaleplon in form V characterized by x-ray diffraction peaks at 8.0, 14.8, and 17.0±0.2 degrees two-theta.

In still yet another aspect, the present invention relates to zaleplon in form V characterized by x-ray diffraction peaks at 8.0, 14.8, and 17.0±0.2 degrees two-theta and further characterized by x-ray diffraction peaks at 10.7, 11.0, 12.5, 15.4, 16.5, 17.7, 21.3, 25.7, and 26.5±0.2 degrees two-theta.

In another aspect, the present invention provides a process for making zaleplon in crystal Form II including the steps of: forming a solution of zaleplon in an organic solvent that is miscible or appreciably soluble in water; contacting the solution with water to induce crystallization of zaleplon, and separating zaleplon Form I from the organic solvent and water.

In another aspect, the present invention provides a process for making zaleplon in crystalline Form II including the steps of: forming a solution of zaleplon in an organic solvent that is miscible with or appreciably soluble in water, contacting the solution with three times its volume of water, optionally cooled to about 0° C., to induce crystallization of zaleplon, and separating zaleplon Form II from the organic solvent and water.

In another aspect, the present invention provides a process for making crystalline zaleplon in Form III including the steps of: forming a solution of zaleplon in acetonitrile, adding water to the solution at elevated temperature, precipitating zaleplon from the solution by cooling, and separating zaleplon Form III from the acetonitrile and water.

In still a further aspect, the present invention provides a process for preparing crystalline zaleplon in Form IV including the steps of: forming a solution of zaleplon in a solvent system selected from the group consisting of 2-propanol and mixtures of tetrahydrofuran and water, precipitating zaleplon from the solution, and separating zaleplon Form IV from the solvent system.

The present invention further provides novel processes for making a known crystalline form of zaleplon.

Thus, in one aspect, the present invention provides a process for preparing zaleplon in Form I including the steps of: forming a suspension of zaleplon in a liquid at elevated temperature, which liquid can be boiling water or a high boiling hydrocarbon, to mention just two, cooling the suspension, and separating zaleplon Form I from the liquid.

In another aspect, the present invention provides a process for making zaleplon in Form I including the steps of: melting zaleplon, solidifying the zaleplon by cooling, and grinding the solidified zaleplon to yield zaleplon Form I.

In still a further aspect, the present invention provides a process for making crystalline zaleplon in form I including the steps of: Dissolving zaleplon in an organic solvent by heating, optionally adding an apolar organic antyisolvent to the resulting solution, inducing precipitation of zaleplon by cooling, and separation of zaleplon Form I.

In yet still a further aspect, the present invention relates to a process for preparing zaleplon in Form I including the steps of: dissolving zaleplon in an organic solvent by heating, addition of an apolar organic antisolvent to the solution, inducing precipitation of zaleplon by cooling, and separation of zaleplon Form I.

Pharmaceutical compositions containing any of the crystal forms of zaleplon herein described—alone or in any combination—are also provided, as are methods of treating, for example, insomnia using any of these pharmaceutical compositions.

In still another aspect, the present invention provides HPLC methods for the analysis and assay of zaleplon.

In another aspect, the present invention provides a HPLC method of assaying zaleplon including the steps of: dissolving zaleplon sample in acetonitrile:water (1:1) diluent, injecting the sample solution (ca. 10 µl) onto a 100 mm×4 mm, 3 Jim RP-18 HPLC column, eluting the sample from the column at 1 ml/min. using a mixture of acetonitrile (28 vol-%) and ammonium-format buffer (72 vol-%, 0.005 M, pH=4) as eluent, and measuring the zaleplon content of the relevant sample at 245 nm wavelength with a UV detector.

DESCRIPTION OF THE PREFERRED EMBODIMENTS

The present invention provides a process that is especially adapted for increasing the purity of a crude zaleplon that can be in mixture with zaleplon regioisomer and other impurities. The present invention also provides a process for enriching such mixtures in regioisomer (5), thereby facilitating the isolation of regioisomer in yet another embodiment of the present invention.

Crude zaleplon useful in the several embodiments of the present invention may be provided as a condensed, unpurified or partially purified end product of a chemical synthesis such as those described in U.S. Pat. Nos. 4,626,538, 5,714, 607 and U.S. patent application Ser. No. 10/170,673, or from any source.

The compound N-[3-(3-cyanopyrazolo[1,5-a]pyrimidin-5-yl)phenyl]-N-ethylacetamide (5), regioisomer of zaleplon, has been discovered as a main impurity in the synthesis of zaleplon starting from 3-amino-4cyanopyrazole and N-[3-[3-(dimethylamino)-1-oxo-2-propenyl]phenyl]-N-ethylacetamide. Under the reaction conditions disclosed in the United States Provisional Patent Application 60/297, 635, the amount of the regioisomer impurity is about 0.2–0.5% (HPLC) in the crude product. The amount of this impurity is strongly dependent on the reaction conditions and, as described hereinbelow, the reaction conditions can be manipulated to maximize the amount of regioisomer formed, thereby facilitating its isolation and characterization.

Thus, in another embodiment, the present invention provides a method for the preparation of the novel N-[3-(3-cyanopyrazolo[1,5-a]pyrimidin-5-yl)phenyl]-N-ethylacetamide (5) starting from 3-amino-4-cyanopyrazole and N-[3-[3-(dimethylamino)-1-oxo-2-propenyl]phenyl]-N-ethylacetamide by reacting them in the presence of an acid in water or in a mixture of water and a water miscible organic solvent in the presence of an acid. The amount of regioisomer (5) can be increased up to 5% (HPLC) by use of a high concentration of a strong acid in the synthesis. This facilitates the isolation and characterization of this new compound.

The reaction can be performed at 20° to 30° C., or at higher temperature up to the boiling point of water. A temperature of 20° to 30° C. is preferred. As a water miscible organic solvent both polar protic (e.g. acetic acid, methanol, ethanol, i-propanol) or polar aprotic (e.g. acetonitrile, tetrahydrofuran, dimethylformamide) solvents can be used. As acid, both mineral (e.g. hydrochloric, sulfuric, phosphoric) and organic (e.g. acetic, trifluoroacetic, methanesulfonic) can be used. Hydrochloric acid is the preferred acid.

In a preferred embodiment, the reaction is performed in water in the presence of hydrochloric acid at about 25° C. Isolation of the mixture of zaleplon and its regioisomer (5) can be performed by evaporation, filtration, extraction or by any combination of these methods.

In a particularly preferred embodiment, after completion of the reaction, the reaction mixture is diluted with water and the precipitated zaleplon is removed by filtration. Then the filtrate is neutralized to precipitate the mixture of zaleplon and its regioisomer 5. A further crop of the mixture can be obtained by extraction of water phase with water immiscible organic solvents such as ethylacetate, dichloromethane, chloroform and like.

Isolation of compound 5 can be performed by chromatography. Column chromatography, preparative TLC or HPLC can be applied. Column chromatography is preferred. As a packing, silica gel or aluminium oxide can be used. Silica gel is the preferred packing. As eluent, various organic solvents or mixtures of them can be used. Mixtures of dichloromethane and acetone are preferred as column eluent. A 3:1 (v:v) mixture of dichloromethane:acetone is particularly preferred as eluent.

Isolated 5 was characterized, and its structure proved, by $^1$H-NMR and $^{13}$C-NMR spectroscopy, as well as by mass spectrometric investigations.

Figure 2:
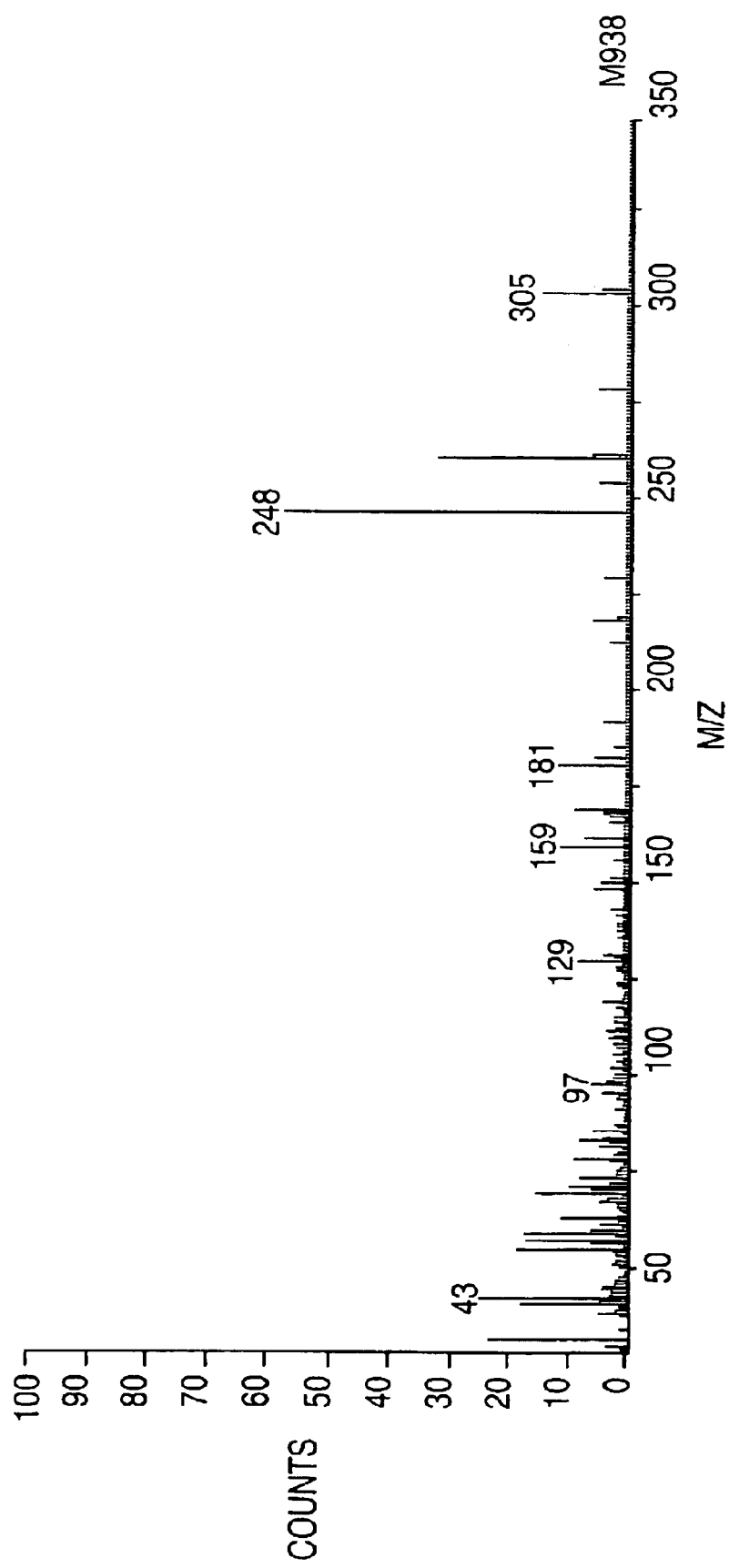
FIG. 2 is a representative mass spectrum of the zaleplon regioisomer.
Figure 3:
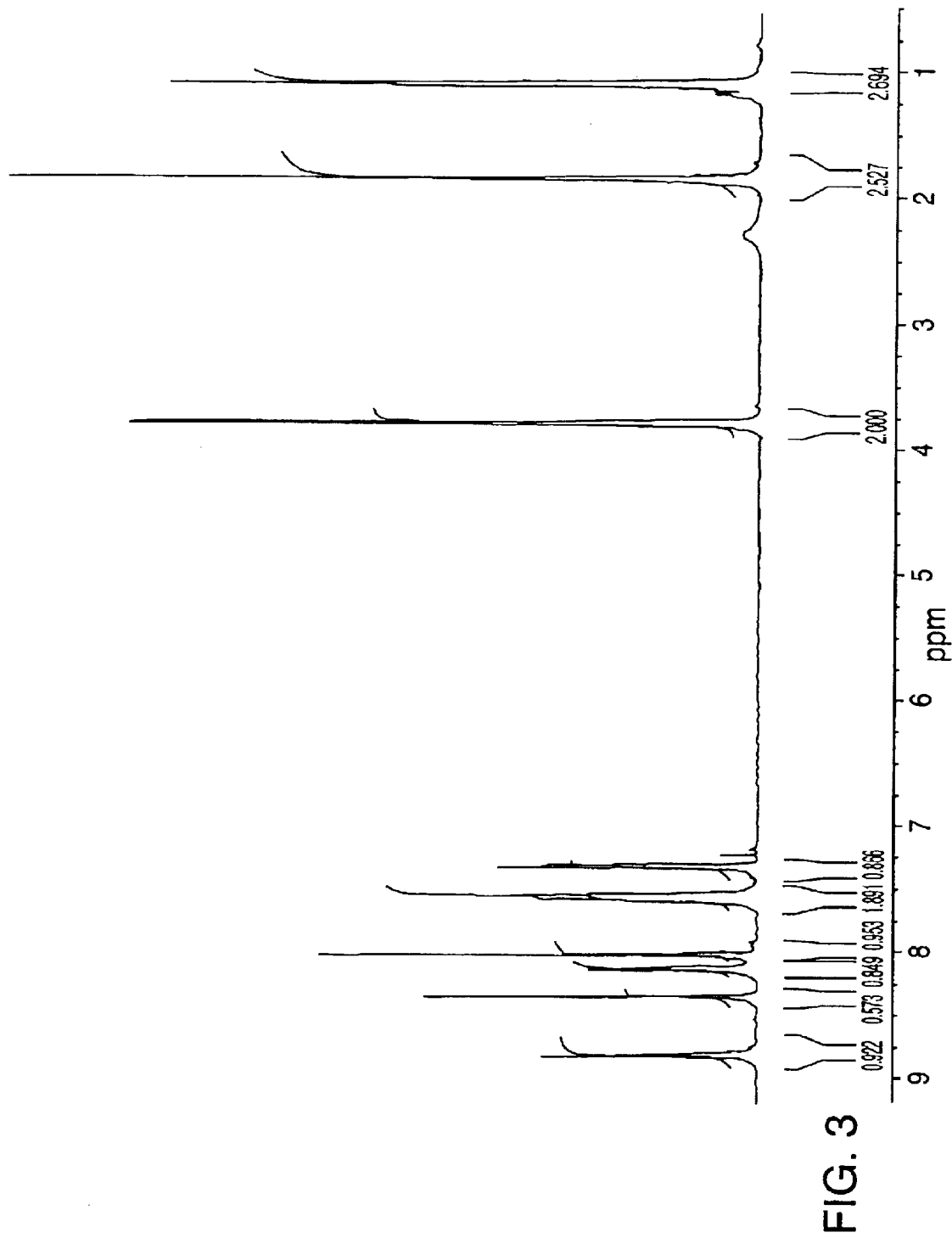
FIG. 3 is a representative 1H NMR spectrum of the zaleplon regioisomer.

FIG. 1 shows the $^{13}$C NMR spectrum of 5. The low-resolution EI mass spectrum of regioisomer 5 is shown in FIG. 2. The $^1$H NMR of regioisomer 5 is shown in FIG. 3. The $^1$H and $^{13}$C NMR peak assignments for 5 are given below.

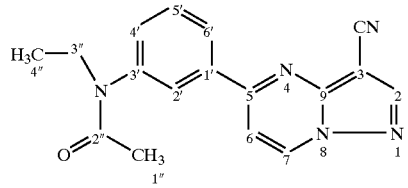

TABLE 1

$^1$H NMR Resonance Assignments

| chemical shift (ppm) | multiplicity | intensity | assignment |
|---|---|---|---|
| 1.143 | triplet | 3H | 4"-CH$_3$(Et) |
| 1.876 | singlet | 3H | 1"-CH$_3$ |
| 3.804 | quadruplet | 2H | 3"-CH$_2$(Et) |
| 7.361 | doublet | 1H | 4'-CH |
| 7.532 | doublet | 1H | 6-CH |
| 7.613 | triplet | 1H | 5'-CH |
| 8.018 | singlet | 1H | 2'-CH |
| 8.159 | doublet | 1H | 6'-CH |
| 8.375 | singlet | 1H | 2-CH |
| 8.805 | doublet | 1H | 7-CH |

TABLE 2

$^{13}$C resonance assignments

| chemical shift (ppm) | assignment |
|---|---|
| 12.89 | 4"-CH$_3$ |
| 22.68 | 1"-CH$_3$ |
| 43.84 | 3"-CH$_2$ |
| 83.17 | 3-C |
| 107.71 | 6-CH |
| 112.84 | CN |
| 127.17 | 6'-CH |
| 127.48 | 2'-CH |
| 130.62 | 5'-CH |
| 131.63 | 4'-CH |
| 136.67 | 7-CH |
| 137.46 | 1'-C |
| 144.1 | 3'-C |
| 148.31 | 2-CH |
| 149.99 | 9-C |
| 158.6 | 5-C |
| 169.9 | 2"-CO |

In accordance with another embodiment of the invention, zaleplon is purified by precipitation under controlled conditions from a solution prepared from a crude zaleplon than can contain zaleplon regioisomer. Impure a crude zaleplon may be subjected to a single iteration of the process to obtain more highly pure zaleplon or the process may be repeated to obtain zaleplon in any desired accessible purity level, including zaleplon essentially free of regioisomer.

In the purification process of the present invention, a solid enriched in zaleplon is precipitated from a solution including an organic solvent. Organic solvents include alcohols, such as methanol, ethanol and 2-propanol; ketones, such as acetone, methyl ethyl ketone and methyl isobutyl ketone; ethers, such as tetrahydrofuran (THF), diethyl ether and methyl t-butyl ether; carboxylic acids, such as acetic acid and propionic acid; carboxylic acid esters, such as ethyl acetate and isobutyl acetate; nitriles, such as acetonitrile and acrylonitrile; aromatic hydrocarbons, such as benzene, toluene and xylenes and halogenated hydrocarbons, such as dichloromethane and chloroform, and mixtures thereof. Optionally, water can be combined with the organic solvent. It will be understood that the organic solvent is selected with reference to its freezing point and the temperature(s) at which the process is performed so that the solvent will not freeze. Generally, preferred organic solvents are acetic acid, methanol, ethanol, 2-propanol, tetrahydrofuran (THF), acetonitrile, acetone, ethyl acetate, toluene and dichloromethane.

The optimal concentration of zaleplon in the solution generally is in a range of from about 100 mM to about 1M, more preferably from about 100 mM to about 700 mM. The organic solvent may be heated to an elevated temperature to obtain a homogeneous solution of the crude zaleplon mixture. As used herein, the term "elevated temperature" means a temperature above about 25° C. Using an organic solvent that boils at the desired temperature is a matter of convenience. Solutions saturated with zaleplon at the temperature at which the solution is formed tend to separate zaleplon from regioisomer 5 as effectively as unsaturated solutions. Forming a saturated solution is preferred.

After the crude zaleplon has completely dissolved, precipitation of a solid enriched in zaleplon from the solution can be induced by cooling. Cooling includes both active cooling by placing an external heat sink where heat exchange can occur between the solution and the heat sink or passive cooling by cessation of active heating. Preferably, the solution is cooled to a reduced temperature, more preferably, to about 5–10° C. Precipitation can also be induced with the aid of an antisolvent, optionally with cooling. As used herein, the term "reduced temperature" means a temperature below about 20° C.

Cooling causes precipitation of a solid enriched in zaleplon relative to the crude zaleplon/regioisomer mixture.

After precipitating the solid enriched in zaleplon from the solution, the solid is separated from the solution depleted of zaleplon to obtain purified zaleplon. Separating can be by any conventional technique for removing a solid from a liquid, such as by filtering or decanting. Further, separating optionally includes conventional washing and drying of the solid, such as is illustrated in the examples.

In one embodiment of the purification process, an antisolvent is added to the solution. An antisolvent, as that term is used in this disclosure, means any liquid in which zaleplon is no more than sparingly soluble and which does not form a separate liquid phase during the process. Preferred antisolvents include aliphatic hydrocarbons and water, with pentane, hexane, heptane, octane, petroleum ether and water being more preferred, hexane and water being most preferred. The ratio of antisolvent to organic solvent is preferably from about 1:1 to about 4:1, more preferably about 1:1 to about 2:1.

When an aliphatic hydrocarbon antisolvent is used, preferred organic solvents are acetic acid, methanol, ethanol, 2-propanol, THF, acetonitrile, acetone, ethyl acetate, toluene and dichloromethane. Preferred organic solvents when the antisolvent is water are acetic acid, methanol, ethanol, 2-propanol, THF, acetonitrile and acetone.

When using an antisolvent, it is preferable to work at a lower concentration range. The preferred concentration range of zaleplon in the organic solvent when an antisolvent is to be added is from about 100 mM to about 400 mM. The antisolvent is preferably added to the solution before the appearance of cloudiness or a precipitate, more preferably the antisolvent is added at elevated temperature.

The antisolvent can be used to assist in forming a saturated or nearly saturated solution without having to remove excess undissolved solids. An unsaturated solution of zaleplon and the regioisomer is formed in the organic solvent. The antisolvent is added to the solution until zaleplon begins to precipitate. Then, the temperature is increased and/or additional organic solvent is added until the precipitated zaleplon goes into solution again, and the purification process is continued by precipitating zaleplon from the so-formed solution.

In especially preferred embodiments, a single iteration of the purification process can reduce the regioisomer content of a crude zaleplon by 50% or more, and even 70% or more. Such reduction is highly effective considering the structural similarity between zaleplon and regioisomer 5. A single iteration of the purification process can reduce the proportion of regioisomer from a value of about 0.2% in crude zaleplon to about 0.03% in solid enriched zaleplon, which amounts to removal of 84% of the regioisomer. Further reduction in the amount of the regioisomer can be achieved by repeating the purification process.

Using an antisolvent can increase the recovery of zaleplon without substantially diminishing the degree of the separation. As demonstrated in the Examples, using an antisolvent in combination with a representative selection of organic solvents uniformly increased recovery of zaleplon.

By means of the purification process of the invention, zaleplon with less than 0.033% regioisomer (according to the HPLC method of the present invention) can be obtained.

Thus, in another embodiment the present invention provides zaleplon having a purity of at least about 98.5% and most preferably at least about 99%. As used herein, percent purity refers to area percent purity determined by the HPLC method herein described. Thus zaleplon of 99% purity (or 99% pure zaleplon) means that the ratio of the HPLC peak area for zaleplon to the sum of all HPLC peak areas, times 100, is 99.

Some embodiments of the purification process were found to produce novel crystalline forms of zaleplon. The stepwise procedure of the purification process can be used to prepare the new forms from pure or impure zaleplon. The new forms also may be accessible by any number of other techniques arrived at empirically.

Figure 4:
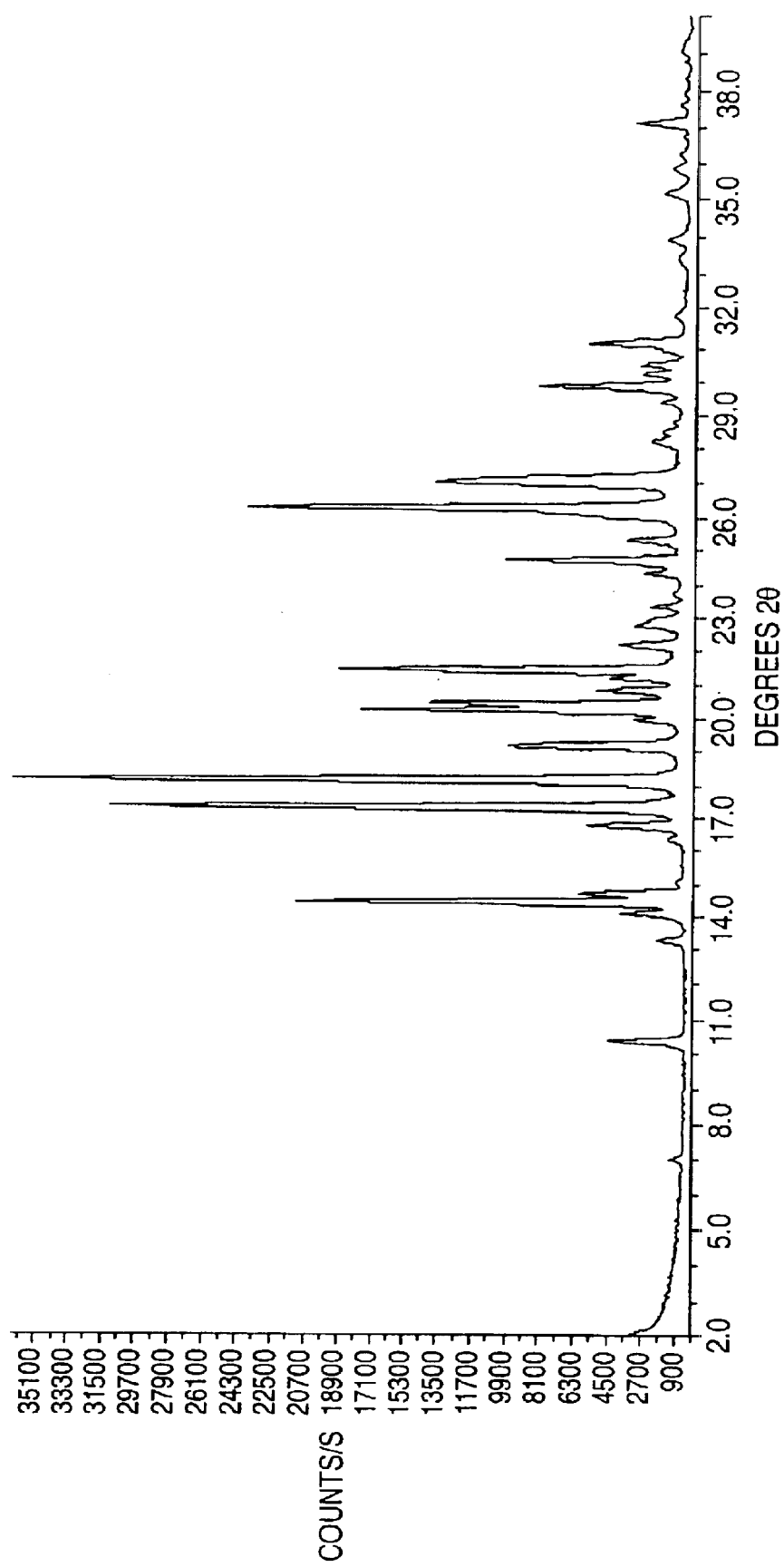
FIG. 4 depicts a powder X-ray diffractogram of zaleplon Form I.

The new forms are distinguishable from the zaleplon that is available in Sonata® by characteristics of their X-ray diffraction patterns. The zaleplon that is in Sonata® is designated Form I in this disclosure. Zaleplon Form I has characteristic peaks in its powder X-ray diffraction pattern (FIG. 4) at 10.5, 14.5, 16.8, 17.3, 18.0 (strong), 19.0, 20.1, 21.3, 24.4, 25.9, 26.7, 29.4, 30.7±0.2 degrees two-theta.

Zaleplon Form II can be prepared following the stepwise procedure of the purification process by using ice water as an antisolvent and a water-miscible or substantially water soluble organic solvent. In particular, zaleplon Form II may be prepared by dissolving zaleplon in a substantially water soluble or water-miscible organic solvent selected from among those previously described. Preferred organic solvents for producing Form II zaleplon are acetic acid, methanol, ethanol, 2-propanol, THF, acetonitrile and acetone. Zaleplon Form II can be precipitated at any temperature, but the temperature is conveniently ambient or elevated. To optimize the recovery of zaleplon, it is preferred to saturate the organic solvent with zaleplon at elevated temperature. Ice water is then added to the mixture. The ratio of the organic solvent and ice water can be from about 1:2 to about 1:5 (v/v), with about 1:3 (v/v) being preferred. Although adding ice water will cool the mixture, the organic solvent/water mixture preferably is further cooled to about 5–10° C. if necessary. The mixture should be stirred while water is added and the mixture is cooled. Under the preferred conditions, crystallization of Form II is substantially complete in about an hour or less, whereupon it can be separated, including optional washing and drying, to obtain crystalline zaleplon Form II.

Figure 5:
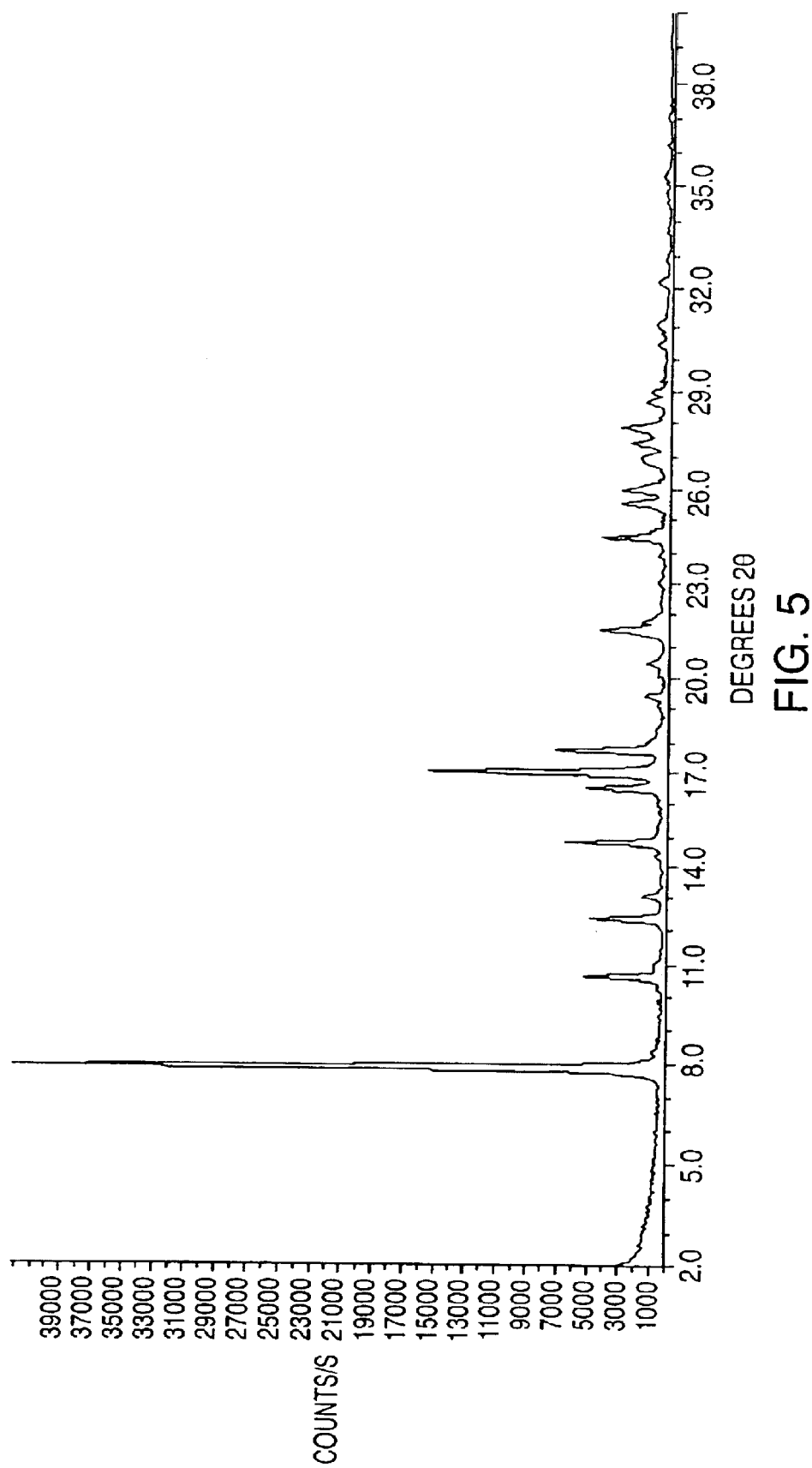
FIG. 5 depicts a powder X-ray diffractogram of zaleplon Form II.
Figure 6:
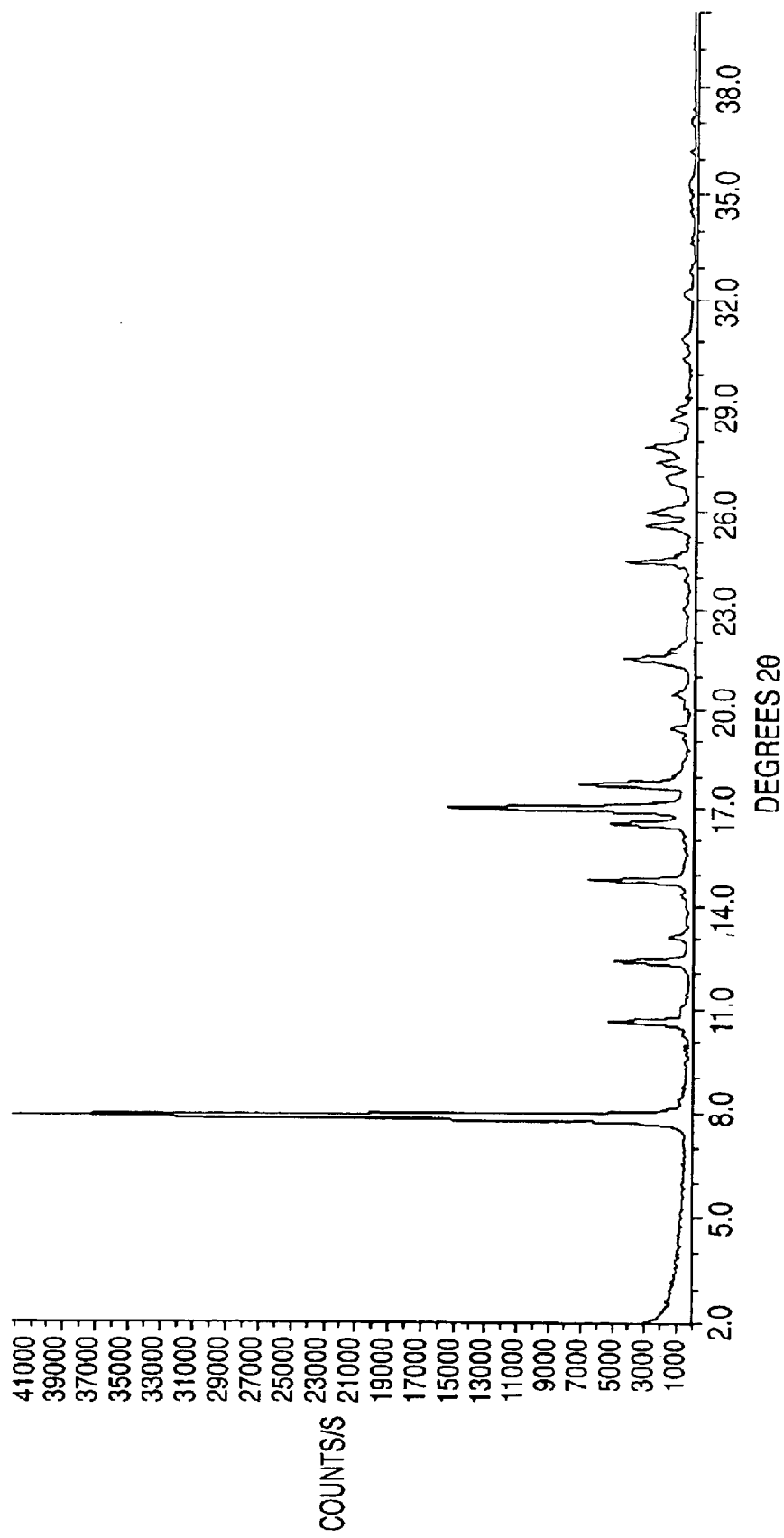
FIG. 6 depicts a powder X-ray diffractogram of zaleplon Form II.

Zaleplon Form II is characterized by a powder X-ray diffraction pattern (FIG. 5) having characteristic peaks at 7.9 (strong), 10.7, 12.5, 14.9, 16.9, 17.9, 21.3, 24.0, 25.2, 25.9, 27.0 and 27.5±0.2 degrees two-theta. This and other PXRD patterns shown in the figures were produced on a Scintag X-ray powder diffractometer model X'TRA equipped with a copper anode tube and a solid state detector. Samples were prepared by gentle and thorough grinding in an agate mortar to reduce preferential orientation. No loss in crystallinity of samples prepared by grinding was noted. The powdered sample was poured into the round cavity of a sample holder and pressed with a glass plate to form a smooth surface. Continuous scans were run from 2 to 40°2θ. at 3° min.$^{-1}$. Reported peak positions are considered accurate to within ±0.050°. Those skilled in the art of X-ray crystallography will appreciate that peak positions determined on different instruments may vary by as much as ±1°.

Zaleplon Form III can be prepared by dissolving zaleplon in refluxing acetonitrile, adding water to the refluxing solution in an amount of from about 2:1 (v/v) to about 4:1 (v/v), preferably about 3:1 (v/v), relative to the acetonitrile, and cooling the mixture to about 5–10° C. without stirring.

Zaleplon Form III was characterized by PXRD spectroscopy and was found to have characteristic peaks in the diffraction pattern at 15.4, 18.1, 19.0, 21.1, 26.8, and 27.5±0.2 degrees two-theta.

Zaleplon Form III is further characterized by peaks in the x-ray diffraction at 11.6, 17.6, 19.0, 20.0, and 22.2±0.2 degrees two-theta.

A novel crystalline form of zaleplon designated Form IV can be prepared by forming a solution of zaleplon in a 1:1 (v/v) mixture of water and THF at reflux, and cooling the solution to room temperature without stirring. Separating the precipitated solid yields zaleplon Form IV. Form IV also can be prepared by forming a solution of zaleplon in 2-propanol at reflux, cooling the solution to 5–10° C. without stirring and separating the precipitated solid.

Figure 7:
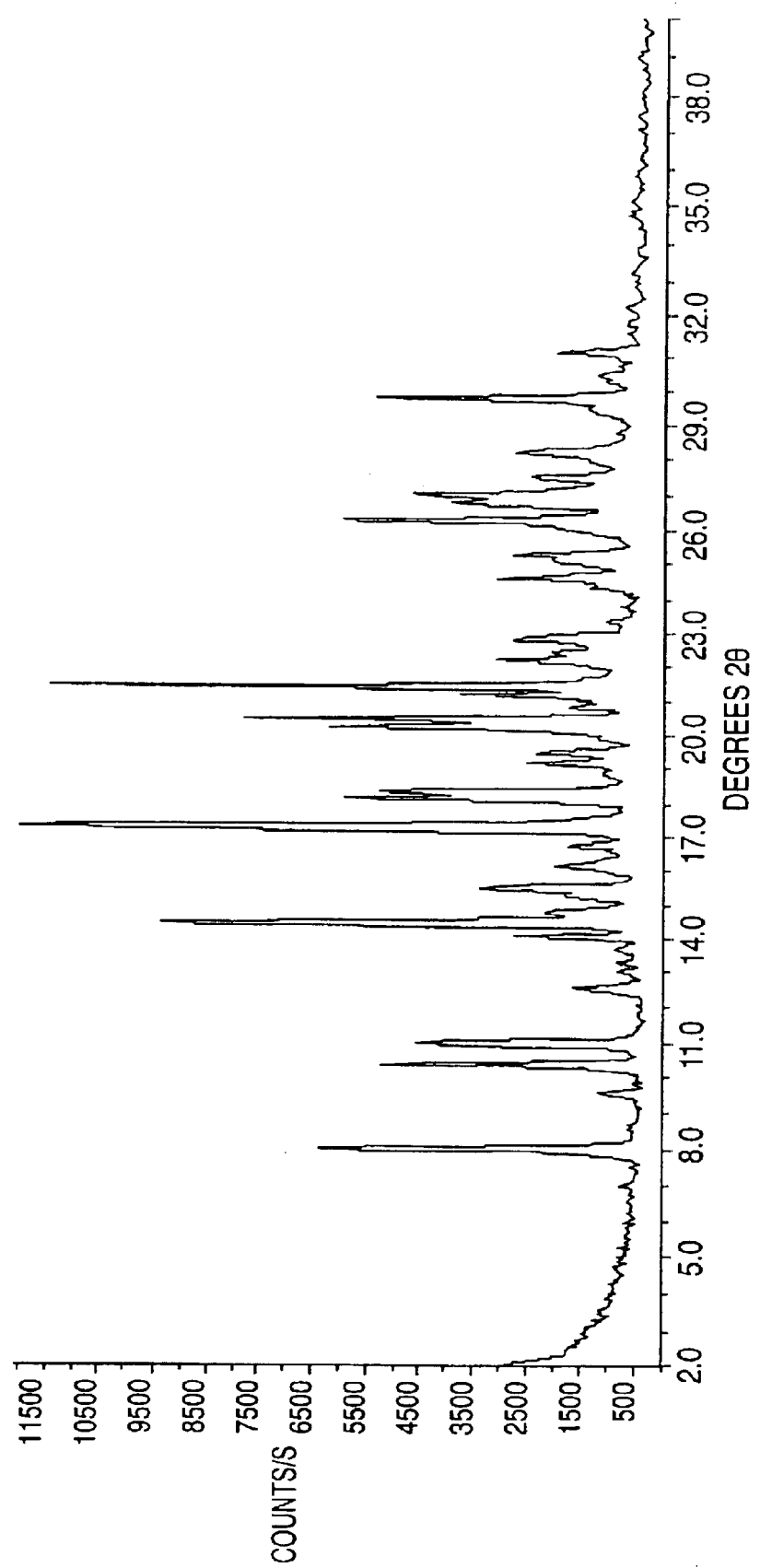
FIG. 7 depicts a powder X-ray diffractogram of zaleplon Form IV.

Zaleplon Form IV was characterized by PXRD spectroscopy and was found to have characteristic peaks in the diffraction pattern (FIG. 7) at 8.1, 14.5, 17.3, 21.3, 24.3, 25.0, 25.9, 26.7, 27.9, 29.5±0.2 degrees two-theta.

Zaleplon Form IV can be further characterized by peaks in the x-ray diffraction diagram at 10.6, 11.1, 14.1, 15.6, 18.0, 18.2, 20.1, 20.3, 24.3, 25.0, 25.9, 26.7, 27.9, and 29.5±0.2 degrees two-theta.

Yet another novel crystalline form of zaleplon, Form V, is obtained by following the Examples in U.S. patent application Ser. No.10/170,673 which has been incorporated by reference in its entirety.

Figure 8:
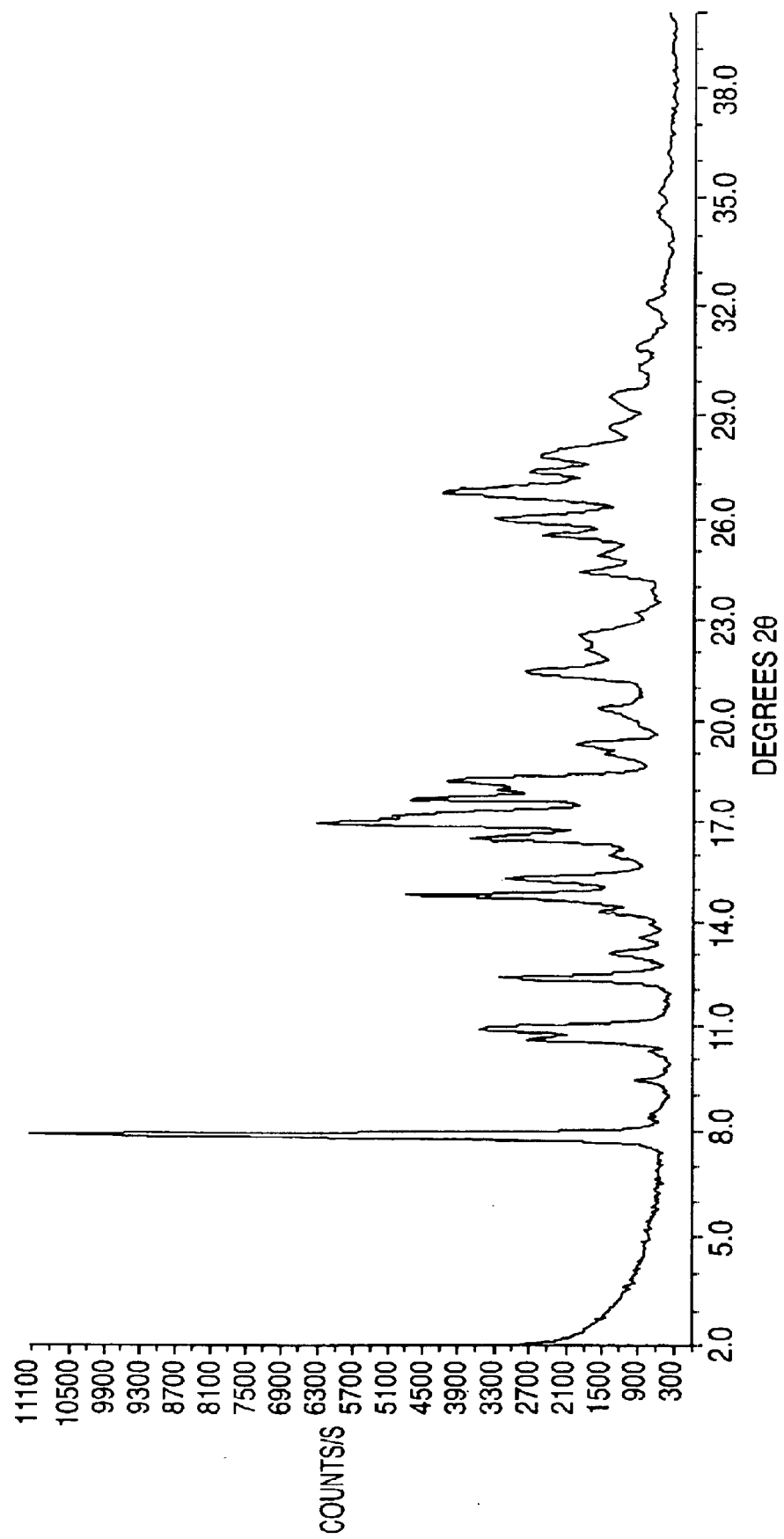
FIG. 8 depicts a powder X-ray diffractogram of zaleplon Form V.

Zaleplon Form V was characterized by PXRD spectroscopy and was found to have characteristic peaks in the diffraction pattern (FIG. 8) at 8.0, 14.8, and 17.0±0.2 degrees two-theta.

Zaleplon Form V can be further characterized by x-ray diffraction peaks at 10.7, 11.0, 12.5, 15.4, 16.5, 17.7, 21.3, 25.7, and 26.5±0.2 degrees two-theta.

The invention further provides novel processes for preparing known zaleplon Form I. In one process for making crystalline zaleplon Form I, zaleplon is suspended in water and refluxed. The suspension is then cooled to room temperature. The crystals are filtered and dried to yield crystalline zaleplon Form I.

According to another process for making zaleplon Form I, zaleplon is slurried in high boiling hydrocarbons. Hydrocarbons are selected from toluene, xylenes, tetrahydronaphthalene and the like. A suitable temperature can be a temperature from about 100° C. to the melting point of zaleplon. After treatment at high temperature the suspension is then cooled to room temperature. The crystals are filtered and dried to yield crystalline zaleplon Form I.

According to another embodiment of the process for making zaleplon Form I, zaleplon is melted and the melted zaleplon is cooled to room temperature and ground to yield crystalline zaleplon Form I.

Novel zaleplon Forms II, III, IV and V are useful for delivering zaleplon to the gastrointestinal tract, mucus membranes and circulatory system of a patient suffering from insomnia. They can be formulated into a pharmaceutical product like Sonata® or another dosage form.

Pharmaceutical compositions of the present invention contain zaleplon Forms II, III, IV and V, optionally in mixture with other forms or amorphous zaleplon and/or other active ingredients. In addition to the active ingredient(s), the pharmaceutical compositions of the present invention may contain one or more excipients. Excipients are added to the composition for a variety of purposes Diluents increase the bulk of a solid pharmaceutical composition and may make a pharmaceutical dosage form containing the composition easier for the patient and caregiver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from punches and a die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, mentho citric acid, fumaric acid, ethyl maltol, and tartaric acid.

Solid and liquid compositions also may be dyed using any pharmaceutically acceptable colorant to improve their appearance and/or facilitate patient identification of the product or unit dosage level.

In liquid pharmaceutical compositions of the present invention, Forms II, III, IV and V and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention also may contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention also may contain a buffer such as guconic acid, lactic acid, citric acid or acetic acid, sodium guconate, sodium lactate, sodium citrate or sodium acetate.

Selection of excipients and the amounts to use maybe readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

The active ingredient and excipients may be formulated into compositions and dosage forms according to methods known in the art.

Capsules, tablets and lozenges and other solid unit dosage forms preferably contain a dosage level of from about 5 to about 20 mg, more preferably from about 5 mg to about 10 mg of zaleplon.

In yet another embodiment, the present invention provides novel gradient elution HPLC method for determination of the impurity profile zaleplon, that is for quantifying, by area percent, the amounts of impurities present in a sample of zaleplon. In this embodiment, suitable for complete resolution (separation) of the peak of zaleplon (1) from the peak of structurally very similar compound (5), as well as from the other impurities, the present invention provides a HPLC method including the steps of:

a, dissolving zaleplon sample in acetonitrile:water (1:1) diluent, b, injecting the sample solution (ca. 10 µl) onto a 250 mm×4.6 mm, 5 µm RP-18 HPLC column, c, gradient eluting at 1 ml/min with a mixture of acetonitrile (A) and ammonium-formate buffer (B, 0.005 M, pH=4) according to the following profile:

| Time (min) | HPLC Gradient | |
|---|---|---|
| | Eluent A (%) | Eluent B (%) |
| 0 | 20 | 80 |
| 11 | 32 | 68 |
| 17 | 40 | 60 |
| 30 | 40 | 60 |
| 31 | 20 | 80 |
| 35 | 20 | 80 | d, measuring of the amounts of each impurity at 245 nm wavelength with a UV detector and appropriate recording device.

Figure 9:
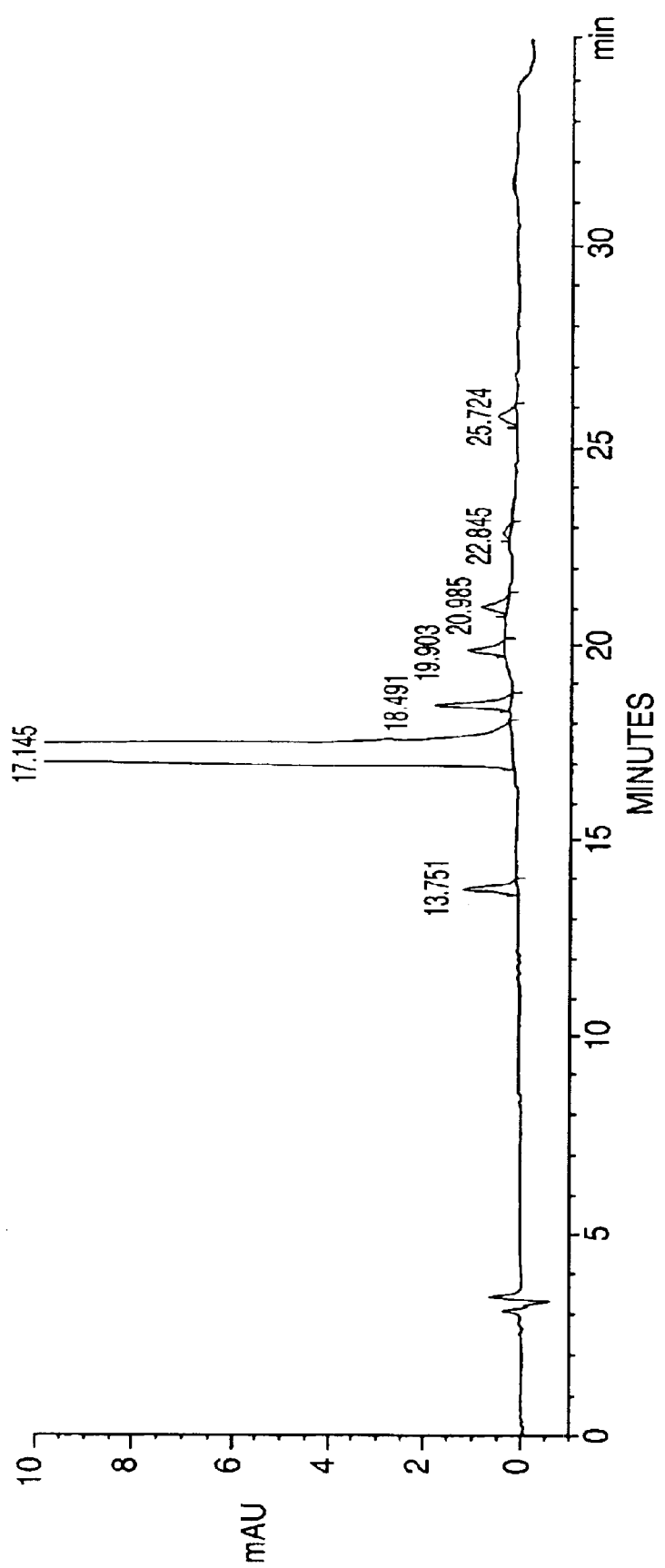
FIG. 9 is a representative HPLC chromatogram of zaleplon obtained using the HPLC method of the present invention.
Figure 10:
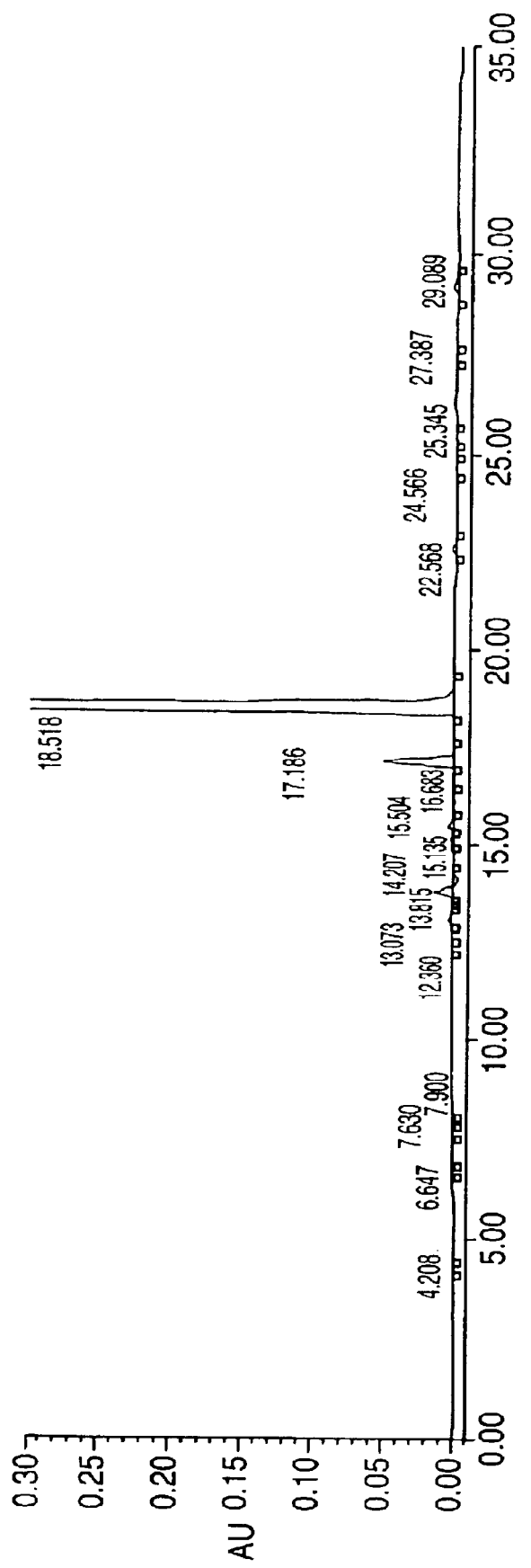
FIG. 10 is a representative HPLC chromatogram of the regioisomer obtained using the methods of the present invention.

In the above method, zaleplon has a retention time of about 17 minutes. A typical HPLC chromatogram using this method is shown in FIG. 9.

In another embodiment, adapted to assay of zaleplon and its main impurity 5 in a drug substance and pharmaceutical compositions containing zaleplon, the present invention provides an isocratic HPLC assay method including the steps of:

a, dissolving zaleplon sample in acetonitrile:water (1:1) diluent, b, injecting the sample solution (ca 10 μl) onto a 100 mm×4 mm, 3 μm RP-18, HPLC column, c, eluting the sample from the column at 1 ml/min using a mixture of acetonitrile (28 vol-%) and ammonium-format buffer (72 vol-%, 0.005 M, pH=4) as eluent, and d, measuring the zaleplon content of the sample at 245 nm wavelength with a UV detector and appropriate recording apparatus In this method, zaleplon has a retention time of about 5 min.

Carbon-13 NMR spectra and proton NMR spectra were obtained at 125 MHz and 500 MHz, respectively, using a Brucker Model DRX spectrometer. The temperature of measurement was 27° C.

Low resolution EI mass spectra were obtained with a VG-7035 mass spectrometer (VG Analytical, Manchester, England). The ionization energy was 70 eV, the ion current was 200 μA. The source temperature was 150°. Theoretical MW=305.127; m/Z found=305.128.

Having thus described the various aspects of the present invention, the following non-limiting examples are provided to illustrate specific embodiments.

EXAMPLES

General

Ethylacetamide 3 was used as received from Precise Chemipharma PVT. Ltd. 3-Amino-4-cyanopyrazole 4 was used as received from Precise Chemipharma PVT. Ltd. Phosphoric acid (85%) was used as received from Aldrich Chemical Co. Organic solvents and antisolvents were used as received.

Zaleplon and regioisomer 5 in the crude zaleplon (i.e. starting mixture) and precipitated products were quantitated by HPLC using UV detection at a wavelength of 254 nm, at which wavelength the response factor of zaleplon and its regioisomer 5 are the same.

Preparation 1

Preparation of a Mixture of Zaleplon and Regioisomer 5

Ethylacetamide 3 (260 g, 1 mol) and 3-amino-4-cyanopyrazole 4 (108 g, 1 mol) were dissolved in a mixture of water (7 L) and ethanol (4 L). Eighty five percent aqueous phosphoric acid (67 ml, 1 mol) was added and the mixture was stirred at room temperature for 8 h. The reaction mixture was then cooled to 5° C. and the crystalline product that formed was collected, washed with water and dried at 60° C. to afford zaleplon (275 g, 90.2%) which was 99.36 pure by HPLC and contained 0.21% regioisomer 5.

Examples 1–8

Purification of Zaleplon by Precipitation

The mixture of zaleplon and regioisomer 5 prepared in Preparation 1 (4 g) was dissolved in refluxing organic solvent. After the zaleplon was completely dissolved, the solution was allowed to cool to room temperature and then was further cooled to 6° C. and maintained at that temperature for 1 day. The resulting crystalline solid was recovered by filtration, washed with the fresh chilled organic solvent from which it was precipitated and dried at 60° C. under vacuum. The separation achieved using different organic solvents is recorded in Table 1.

TABLE 3

| Ex. | Solvent | Volume Solvent (ml) | Yield (%) | Composition of Precipitated Product (HPLC % Area) | | % Regio-isomer 5 Removed |
|---|---|---|---|---|---|---|
| | | | | Zaleplon | Regio-isomer 5 | |
| 1 | Methanol | 40 | 81.3 | 99.790 | 0.077 | 63 |
| 2 | Ethanol | 40 | 88.3 | 99.706 | 0.122 | 42 |
| 3 | 2-Propanol | 40 | 86.3 | 99.661 | 0.108 | 49 |
| 4 | Acetonitrile | 20 | 55.8 | 99.881 | 0.033 | 84 |
| 5 | Acetone | 20 | 52.0 | 99.871 | 0.042 | 80 |
| 6 | THF | 20 | 54.8 | 99.833 | 0.085 | 60 |
| 7 | Ethyl acetate | 60 | 71.5 | 99.802 | 0.079 | 62 |
| 8 | Toluene | 35 | 87.5 | 99.552 | 0.13 | 38 |

Examples 9–21

Precipitation of Zaleplon Using an Antisolvent

The mixture of zaleplon and regioisomer 5 prepared in Preparation 1 (4 g) was dissolved in refluxing organic solvent. After the zaleplon had completely dissolved, antisolvent was slowly added to the refluxing solution. After completing the addition, the mixture was cooled to 5° C. The resulting crystalline solid was recovered by filtration washed with fresh chilled organic solvent from which it was precipitated and dried under vacuum at 60° C. The separation achieved using different organic solvent and antisolvent combinations is recorded in Table 2.

TABLE 4

| Ex. | Solvent | Volume Solvent (ml) | Antisolvent | Volume Antisolvent (ml) | Yield (%) | Composition of Precipitated Product (HPLC % Area) | | % Regioisomer 5 Removed |
|---|---|---|---|---|---|---|---|---|
| | | | | | | Zaleplon | Regioisomer 5 | |
| 9 | Ethyl | 60 | hexane | 120 | 94.3 | 99.533 | 0.138 | 34 |
| 10 | Ethanol | 50 | hexane | 80 | 87.5 | 99.737 | 0.111 | 47 |
| 11 | Acetonitrile | 20 | hexane | 40 | 62.5 | 99.672 | 0.091 | 57 |
| 12 | Acetone | 20 | hexane | 40 | 91.8 | 99.668 | 0.094 | 55 |

TABLE 4-continued

| Ex. | Solvent | Volume Solvent (ml) | Antisolvent | Volume Antisolvent (ml) | Yield (%) | Composition of Precipitated Product (HPLC % Area) | | % Regioisomer 5 Removed |
|---|---|---|---|---|---|---|---|---|
| | | | | | | Zaleplon | Regioisomer 5 | |
| 13 | THF | 20 | hexane | 40 | 91.5 | 99.503 | 0.152 | 28 |
| 14 | 2-Propanol | 40 | hexane | 80 | 91.5 | 99.645 | 0.136 | 35 |
| 15 | Acetic acid | 20 | water | 40 | 83.8 | 99.719 | 0.054 | 74 |
| 16 | Methanol | 40 | water | 80 | 95.8 | 99.702 | 0.080 | 62 |
| 17 | Ethanol | 40 | water | 80 | 93.5 | 99.690 | 0.084 | 60 |
| 18 | Acetonitrile | 20 | water | 40 | 90.0 | 99.752 | 0.040 | 81 |
| 19 | 2-Propanol | 40 | water | 80 | 87.8 | 99.747 | 0.056 | 73 |
| 20 | Acetone | 20 | water | 40 | 89.8 | 99.683 | 0.080 | 62 |
| 21 | THF | 20 | water | 40 | 83.0 | 99.731 | 0.051 | 76 |

Example 22

Preparation of Crystalline Zaleplon Form I

Zaleplon (10 g) was dissolved in refluxing ethanol (100 ml) with stirring. Hexane (200 ml) was added dropwise to the refluxing solution. Then, the mixture was cooled to 5° C. with stirring over about 4 h. The precipitate was collected by filtration to yield crystalline zaleplon Form I (8.9 g, 89%).

Example 23

Preparation of Crystalline Zaleplon Form II

Zaleplon (10 g) was dissolved in acetic acid (50 ml) at 50° C. with stirring. The resulting solution was poured into ice-water (150 ml) to induce immediate precipitation. The precipitate was collected by filtration to yield crystalline zaleplon Form II (8.5 g, 85%).

Example 24

Preparation of Crystalline Zaleplon Form III

Zaleplon (10 g) was dissolved in refluxing acetonitrile (50 ml) with stirring. Water (150 ml) was added dropwise to the refluxing solution. Then, the clear solution was cooled to 5° C. without stirring. The precipitate was collected by filtration to yield crystalline zaleplon form III (9.1 g, 91%)

Example 25

Preparation of Crystalline Zaleplon Form IV

Zaleplon ( g) was dissolved in refluxing 2-propanol (150 ml) with stirring. The clear solution was cooled to 5° C. without stirring. The precipitate was collected by filtration to yield crystalline zaleplon form IV (8.6 g, 86%).

Example 26

Preparation of Crystalline Zaleplon Form I

Zaleplon (26.8 g) is dissolved in the mixture of ethanol and water (210 and 210 cm3) at reflux temperature then treated with charcoal (2.7 g, 10 m/m%). The solution is stirred for 30 minutes at reflux temperature and filtered. The charcoal is washed with a hot mixture of ethanol and water (30:30cm3). The solution is cooled to 25° C. in 6 hours and kept at this temperature for2 hours. Crystals are filtered and washed with the mixture of ethanol and water (20:20 cm3) and dried under vacuum at 60° C. for 8 hours to afford crystalline zaleplon form I (22.8 g, 85%)

Example 27

Preparation of Crystalline Zaleplon Form I

Zaleplon (22.8 g) is dissolved in ethanol (230 cm3) at reflux temperature then treated with charcoal (2.3 g,10 m/m%). The solution is stirred for 10 minutes and filtered. The charcoal is washed with hot ethanol (20 cm3). The solution is cooled to 25° C. in 6 hours and kept at this temperature for 2 hours. Crystals are filtered and washed with ethanol (30 cm3). The product is dried under vacuum at 60° C. for 8 hours to afford zaleplon form I (18.7 g, 82%).

Example 28

Preparation of N-[3-(3-cyanopyrazolo[1,5-a] pyrimidin-5-yl)phenyl]-N-ethyl-acetamide N-[3-[3-(dimethylamino)-1-oxo-2-propenyl]phenyl]-N-ethylacetamide (5.2 g, 0.02 mol) and 3-amino-4cyanopyrazole (2.16 g, 0.02 mol) were dissolved in the mixture of water (50 ml) and concentrated hydrochloric acid (40 ml) and the mixture was stirred at room temperature for 8 h. The reaction mixture was then cooled to 5° C. and the precipitate was removed by filtration. The filtrate was neutralized by concentrated aqueous ammonia solution to precipitate 380 mg of the mixture of zaleplon and its regioisomer 5 which was collected by filtration. The filtrate was extracted with 100 ml of ethylacetate to give 100 mg of the mixture of the above two compounds upon evaporation. The two crops combined were put to a silica gel column (100 g) and the elution was performed by the solvent mixture of chloroform and acetone 3:1 (v/v) to yield as a second crop 240 mg (4%) of 5; mp 194–196° C.; $^1$H-NMR (CDCl$_3$) δ (ppm) 1.143 (t, 3H), 1.876 (s, 3H), 3.804 (q,2H), 7.361 (d, 1H), 7.532 (d, 1H), 7.613 (t, 1H), 8.018 (s, 1H), 8.159 (d, 1H), 8.375 (s, 1H) 8.805 ((d, 1H); $^{13}$C-NMR (CDCl$_3$) δ (ppm) 12.89, 22.68, 43.84, 83.17, 107.71, 112.84, 127.17, 127.48, 130.62, 131.63, 136.67, 137.46, 144.10, 148.31, 149.99, 158.60, 169.90, MS (EI, 70 EV) m/z (%) 305 (M$^+$, 18), 248 (59).

Example 29

Pure Zaleplon Essentially Free of Zaleplon Regioisomer

Crude zaleplon prepared as in Preparation 1 (4 g) is dissolved in refluxing acetonitrile (20 mL). When the zaleplon is completely dissolved, the solution is allowed to cool to a temperature between about 20° C. and about 25° C. The resulting mixture is then cooled to about 6° C. and maintained at that temperature for about 24 hours. The precipitate that is a solid enriched in zaleplon is recovered by filtration and washed with fresh chilled acetonitrile.

The recovered precipitate of solid enriched in zaleplon (ca. 2.3 g) is dissolved in refluxing acetonitrille (ca. 10 mL). The solution is allowed to cool to a temperature between about 20° C. and about 25° C. The resulting mixture is then cooled to about 6° C. and maintained at that temperature for about 24 hours. The precipitate is recovered by filtration, washed with fresh chilled acetonitrile, and dried at 60° C. under vacuum.

The recovered precipitate of further purified zaleplon is analyzed by the gradient HPLC method of the present invention and found to be >99% pure. No regioisomer is detected in the precipitate using the gradient HPLC method of the present invention. The zaleplon is essentially free of regioisomer.

What is claimed is:

1. A process for purifying zaleplon comprising the steps of:
    (a) forming a solution of a solid comprising zaleplon and a regioisomer of zaleplon at elevated temperature in a solvent selected from the group consisting of:
        (1) an organic solvent selected from the group consisting of ethanol, methyl ethyl ketone, methyl isobutyl ketone, diethyl ether, methyl t-butyl ether, propionic acid, ethyl acetate, isobutyl acetate, acrylonitrile, benzene, toluene, xylenes, dichloromethane, chloroform and mixtures thereof, and
        (2) mixtures of said organic solvent and water,
    (b) cooling the solution to induce precipitation of a solid enriched in zaleplon and depleted of the regioisomer relative to the solid comprising zaleplon used to from the solution, and
    (c) isolating the precipitated solid that is enriched in zaleplon and depleted of the regioisomer, wherein the separated precipitate is zaleplon crystalline Form IV.

2. A process for purifying zaleplon comprising the steps of:
    (a) forming a solution of a solid comprising zaleplon and a regioisomer of zaleplon at elevated temperature in a solvent selected from the 1p consisting of:
        (1) an organic solvent selected from the group consisting of ethanol, methyl ethyl ketone, methyl isobutyl ketone, diethyl ether, methyl t-butyl ether, propionic acid, ethyl acetate, isobutyl acetate acrylonitrile, benzene, toluene, xylenes, dichloromethane chloroform and mixtures thereof, and
        (2) mixtures of said organic solvent and water,
    (b) adding an antisolvent to the solution at elevated temperature,
    (c) cooling the solution to induce precipitation of a solid enriched in zaleplon and depleted of the regioisomer relative to the solid comprising zaleplon used to form the solution, and
    (d) isolating the precipitated solid that is enriched in zaleplon and depleted of the regioisomer.

3. The process of claim 2 wherein the antisolvent is an aliphatic hydrocarbon.

4. The process of claim 3 wherein the aliphatic hydrocarbon is hexane and the solvent is ethanol.

5. The process of claim 3 wherein the aliphatic hydrocarbon is hexane.

6. The process of claim 5 wherein the solvent is ethanol and the separated precipitate is crystalline zaleplon Form I.

7. The process of claim 2 wherein the antisolvent is water.

8. A process for purifying zaleplon comprising the steps of:
    (a) forming a solution of a solid comprising and a regioisomer of zaleplon in ethanol,
    (b) precipitating a first solid enriched in zaleplon and depleted of the regioisomer relative to the solid comprising zaleplon used to make the first solution,
    (c) isolating the first solid,
    (d) forming a solution of the first solid in ethanol,
    (e) precipitating a second solid enriched in zaleplon and depleted of the regioisomer relative to the first solid, and
    (f) isolating the second solid.

9. A process for purifying zaleplon comprising the steps of:
    (a) forming a solution of a solid comprising zaleplon in ethanol,
    (b) precipitating a solid enriched in zaleplon, relative to the solid comprising zaleplon used to make the solution, with the use of an antisolvent that is water,
    (c) isolating the precipitated solid that is enriched in zaleplon,
    (d) forming a solution of the precipitated sold enriched in zaleplon of step (c) in ethanol,
    (e) precipitating from the solution of step (d), without the aid of an antisolvent, a solid further enriched in zaleplon relative to the solid enriched in zaleplon of step (c),
    (f) isolating the solid further enriched in zaleplon of step (e).

10. A process for preparing crystalline zaleplon Form III characterized by a powder X-ray diffraction pattern having peaks at 15.4, 18.1, 21.1 26.8, and 27.5±0.2 degrees two-theta comprising:
    (a) forming a solution of zaleplon in acetonitrile,
    (b) adding water to the solution at elevated temperature,
    (c) precipitating zaleplon from the solution by cooling, and
    (d) separating zaleplon Form III from the acetonitrile and water.

11. A process for preparing crystalline zaleplon Form IV characterized by a powder X-ray diffraction pattern having peaks at 8.1, 14.5, 17.3, 21.3±0.2 degrees two-theta comprising the steps of:
    (a) forming a solution of zaleplon in a solvent system selected from the group consisting of 2-propanol and mixtures of tetrahydrofuran and water,
    (b) precipitating zaleplon from the solution, and
    (c) separating zaleplon Form IV from the solvent system.

12. A process for preparing zaleplon Form I comprising the steps of:
    (a) forming a suspension of zaleplon in boiling water at elevated temperature,
    (b) cooling the suspension, and
    (c) separating zaleplon Form I from the water.

13. A process for preparing zaleplon Form I comprising the steps of:
    (a) forming a suspension of zaleplon in a high boiling hydrocarbon at elevated temperature,
    (b) cooling the suspension, and
    (c) separating zaleplon Form I from the high boiling hydrocarbon.

14. A process for preparing zaleplon Form I comprising the steps of
   (a) melting zaleplon,
   (b) solidifying the zaleplon by cooling, and
   (c) grinding the solidified zaleplon to yield zaleplon Form I.

15. A process for preparation of zaleplon Form I comprising the steps of
   (a) dissolving zaleplon in an organic solvent by heating,
   (b) addition of an apolar organic antisolvent to the solution,
   (c) inducing precipitation of zaleplon by cooling, and
   (d) separation of zaleplon Form I.

16. A method of making N-[3-(3-cyanopyrazolo[1,5-a]pyrimidin-5-yl)phenyl]-N-ethylacetamide comprising the steps of
   a, reacting a mixture of N-[3-[3-(dimethylamino)-1-oxo-2-propenyl]phenyl]-N-ethylacetamide, 3-amino-4-cyanopyrazole, and a strong acid in a liquid reaction medium of water and at least one water-miscible organic compound free of carboxylic acid groups,
   b, neutralizing the reaction mixture to precipitate crude product, and
   c, separating N-[3-(3-cyanopyrazolo[1,5-a]pyrimidin-5-yl)phenyl]-N-ethylacetamide from other components of crude product by chromatography on a silica gel column using a mixture of chloroform and acetone as eluent, wherein the amount of strong acid, on a mole basis, is at least 10 times the amount of either N-[3-[3(dimethylamino)-1-oxo-2-propenyl]phenyl]-N-ethylacetamide or 3-amino-4-cyanopyrazole, whichever is in excess, or of either of them if they are used in approximately equimolar amounts.

17. The method of claim 16 wherein the amount of strong acid, on a mole basis, is at least 20 times the amount of either N-[3-[3-(dimethylamino)-1-oxo-2-propenyl]phenyl]-N-ethylacetamide or 3-amino-4-cyanopyrazole, whichever is in excess, or of either of them if used in approximately equimolar amounts.

18. A HPLC method of assaying zaleplon comprising the steps of:
   a, dissolving zaleplon sample in acetonitrile:water (1:1) diluent,
   b, injecting the sample solution (ca. 10 µl) onto a 100 mm×4 mm, 3 µm RP-18 HPLC column,
   c, eluting the sample from the column at 1 ml/min. using a mixture of acetonitrile (28 vol-%) and ammonium-format buffer (72 vol-%, 0.005 M, pH=4) as eluent, and
   d, measuring the zaleplon content of the relevant sample at 245 run wavelength with a UV detector.

19. A HPLC method for quantifying the amount of impurities in zaleplon comprising the steps of:
   a, dissolving zaleplon sample in acetonitrile:water (1:1) diluent,
   b, injecting the sample solution (ca. 10 µl) onto a 250 mm×4.6 mm, 5 µm RP-18 HPLC column,
   c, gradient eluting at 1 ml/min with a mixture of acetonitrile (A) and ammonium-formate buffer (B, 0.005 M, pH=4) according to the following profile:

| Time (min) | HPLC Gradient | |
|---|---|---|
| | Eluent A (%) | Eluent B (%) |
| 0 | 20 | 80 |
| 11 | 32 | 68 |
| 17 | 40 | 60 |
| 30 | 40 | 60 |
| 31 | 20 | 80 |
| 35 | 20 | 80 | d, measuring of the amounts of each impurity at 245 nm wavelength with a UV detector and appropriate recording device.

* * * * *

UNITED STATES PATENT AND TRADEMARK OFFICE
CERTIFICATE OF CORRECTION

PATENT NO. : 6,852,858 B2
APPLICATION NO. : 10/211461
DATED : August 1, 2002
INVENTOR(S) : Erika Feher et al.

It is certified that error appears in the above-identified patent and that said Letters Patent is hereby corrected as shown below:

On the Title of the patent
(57) ABSTRACT, change "v crystallization" to --crystallize--

Column 4
Line 57, change "pyrAzole" to --pyrazole--

Column 6
Line 48, change "methanol ethanol" to --methanol, ethanol--

Column 7
Line 25, change "sold enriched in zaleplon of step in ethanol" to --solid enriched in zaleplon in ethanol--
Line 26, change "preceeding" to --preceding--
Line 29, change "in zaleplon of step." to --in zaleplon.--
Line 59, change "by by" to --by--

Column 8
Line 47, change "antyisolvent" to --antisolvent--
Line 67, change "3 Jim" to --3μ--

Column 9
Line 2, change "ammonium-format" to --ammonium-formate--

Column 10
Line 12, change "5" to --regioisomer 5--
Line 14, change "5" to --regioisomer 5--
Line 15, change "5" to --regioisomer 5--
Line 65, change "than" to --that--
Line 66, change "Impure a crude" to --Impure crude--

Column 14
Line 42, change "purposes" to --purposes.--

Column 15
Line 58, change "alginic acid bentonite" to --alginic acid, bentonite--
Line 60, change "gelatin guar gum" to --gelatin, guar gum--

UNITED STATES PATENT AND TRADEMARK OFFICE
CERTIFICATE OF CORRECTION

PATENT NO. : 6,852,858 B2
APPLICATION NO. : 10/211461
DATED : August 1, 2002
INVENTOR(S) : Erika Feher et al.

It is certified that error appears in the above-identified patent and that said Letters Patent is hereby corrected as shown below:

Column 16
Line 7, change "guconic" to --gluconic--
Line 8, change "guconate" to --gluconate--
Line 28, change "losenges" to --lozenges--

Column 17
Line 3, change "FIG. 9" to --FIG. 9.--
Line 5, change "impurity 5" to --impurity regioisomer 5--
Line 16, change "ammonium-format" to --ammonium-formate--

Column 21
Line 5, change "acetonitrille" to --acetonitrile--
Line 33, change "used to from" to --used to form--
Line 43, change "from the lp consisting of" to --from the group consisting of--

Column 22
Line 3, change "comprising and a" to --comprising zaleplon and a--
Line 35, change "21.1 26.8" to --21.1, 26.8--

Column 24
Line 11, change "ammonium-format" to --ammonium-formate--
Line 13, change "245 run" to --245 nm--

Signed and Sealed this

Eleventh Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 6,852,858 B2
APPLICATION NO. : 10/211461
DATED : February 8, 2005
INVENTOR(S) : Erika Feher et al.

It is certified that error appears in the above-identified patent and that said Letters Patent is hereby corrected as shown below:

On the Title of the patent
(57) ABSTRACT, change "v crystallization" to --crystallize--

Column 4
Line 57, change "pyrAzole" to --pyrazole--

Column 6
Line 48, change "methanol ethanol" to --methanol, ethanol--

Column 7
Line 25, change "sold enriched in zaleplon of step in ethanol" to --solid enriched in zaleplon in ethanol--
Line 26, change "preceeding" to --preceding--
Line 29, change "in zaleplon of step." to --in zaleplon.--
Line 59, change "by by" to --by--

Column 8
Line 47, change "antyisolvent" to --antisolvent--
Line 67, change "3 Jim" to --3µ--

Column 9
Line 2, change "ammonium-format" to --ammonium-formate--

Column 10
Line 12, change "5" to --regioisomer 5--
Line 14, change "5" to --regioisomer 5--
Line 15, change "5" to --regioisomer 5--
Line 65, change "than" to --that--
Line 66, change "Impure a crude" to --Impure crude--

Column 14
Line 42, change "purposes" to --purposes.--

Column 15
Line 58, change "alginic acid bentonite" to --alginic acid, bentonite--
Line 60, change "gelatin guar gum" to --gelatin, guar gum--

UNITED STATES PATENT AND TRADEMARK OFFICE
CERTIFICATE OF CORRECTION

PATENT NO.      : 6,852,858 B2
APPLICATION NO. : 10/211461
DATED           : February 8, 2005
INVENTOR(S)     : Erika Feher et al.

It is certified that error appears in the above-identified patent and that said Letters Patent is hereby corrected as shown below:

Column 16
Line 7, change "guconic" to --gluconic--
Line 8, change "guconate" to --gluconate--
Line 28, change "losenges" to --lozenges--

Column 17
Line 3, change "FIG. 9" to --FIG. 9.--
Line 5, change "impurity 5" to --impurity regioisomer 5--
Line 16, change "ammonium-format" to --ammonium-formate--

Column 21
Line 5, change "acetonitrille" to --acetonitrile--
Line 33, change "used to from" to --used to form--
Line 43, change "from the lp consisting of" to --from the group consisting of--

Column 22
Line 3, change "comprising and a" to --comprising zaleplon and a--
Line 35, change "21.1 26.8" to --21.1, 26.8--

Column 24
Line 11, change "ammonium-format" to --ammonium-formate--
Line 13, change "245 run" to --245 nm--

This certificate supersedes the Certificate of Correction issued March 11, 2008.

Signed and Sealed this

First Day of April, 2008

JON W. DUDAS
*Director of the United States Patent and Trademark Office*